US007557353B2

(12) United States Patent
Black et al.

(10) Patent No.: US 7,557,353 B2
(45) Date of Patent: Jul. 7, 2009

(54) SINGLE-USE EXTERNAL DOSIMETERS FOR USE IN RADIATION THERAPIES

(75) Inventors: Robert D. Black, Chapel Hill, NC (US); Gregory Glenwood Mann, Raleigh, NC (US); Steven R. Widener, Wake Forest, NC (US); Phillip M. Lehman, Raleigh, NC (US)

(73) Assignee: Sicel Technologies, Inc., Morrisville, NC (US)

( * ) Notice: Subject to any disclaimer, the term of this patent is extended or adjusted under 35 U.S.C. 154(b) by 1384 days.

(21) Appl. No.: 10/303,591

(22) Filed: Nov. 25, 2002

(65) Prior Publication Data

US 2003/0125616 A1 Jul. 3, 2003

Related U.S. Application Data

(60) Provisional application No. 60/334,580, filed on Nov. 30, 2001.

(51) Int. Cl.
*G01T 1/02* (2006.01)

(52) U.S. Cl. ................................................ 250/370.07

(58) Field of Classification Search ............. 250/370.07
See application file for complete search history.

(56) References Cited

U.S. PATENT DOCUMENTS 3,229,684 A 1/1966 Nagumo et al.
3,638,640 A 2/1972 Shaw ........................ 128/2 R
3,972,320 A 8/1976 Kalman .................. 128/2.1 A
4,142,383 A 3/1979 Eberhart ....................... 63/23
4,163,380 A 8/1979 Masoner ..................... 72/342
4,326,535 A 4/1982 Steffel et al. ................ 128/631
4,361,153 A 11/1982 Slocum et al. ........... 128/419 P
4,397,313 A 8/1983 Vaguine ..................... 128/399
4,397,314 A 8/1983 Vaguine ..................... 128/399
4,416,283 A 11/1983 Slocum ................ 128/419 PG
4,431,004 A 2/1984 Bessman et al. ............ 128/635
4,475,401 A 10/1984 Punia et al. .................. 73/658

(Continued)

FOREIGN PATENT DOCUMENTS

DE 3332075 A1 9/1982

(Continued)

OTHER PUBLICATIONS

Akin, T., K. Najafi, R.M. Bradley, "An implantable multichannel digital neural recording system for a micromachined sieve electrode," Proc. Int. Conf. on Solid-State Sensors and Actuators, Stockholm, Sweden, vol. 1, pp. 51-54 (Jun. 1995).

(Continued)

*Primary Examiner*—David P Porta
*Assistant Examiner*—Marcus H Taningco
(74) *Attorney, Agent, or Firm*—Myers, Bigel, Sibley & Sajovec, P.A.

(57) ABSTRACT

Methods, systems, devices, and computer program products include positioning disposable single-use radiation sensor patches that have adhesive means onto the skin of a patient to evaluate the radiation dose delivered during a treatment session. The sensor patches are configured to be minimally obtrusive and operate without the use of externally extending power chords or lead wires.

92 Claims, 19 Drawing Sheets

U.S. PATENT DOCUMENTS

| | | | | |
|---|---|---|---|---|
| 4,484,076 | A | 11/1984 | Thomson | 250/370 |
| 4,494,545 | A | 1/1985 | Slocum et al. | 128/1.5 |
| 4,519,401 | A | 5/1985 | Ko et al. | 118/748 |
| 4,523,279 | A | 6/1985 | Sperinde et al. | 364/416 |
| 4,541,901 | A | 9/1985 | Parker et al. | 29/1 T |
| 4,543,953 | A | 10/1985 | Slocum et al. | 128/419 PT |
| 4,554,639 | A | 11/1985 | Baker et al. | 364/556 |
| 4,556,063 | A | 12/1985 | Thompson et al. | 128/419 PT |
| 4,571,292 | A | 2/1986 | Liu et al. | 204/412 |
| 4,571,589 | A | 2/1986 | Slocum et al. | 128/419 PG |
| 4,575,676 | A | 3/1986 | Palkuti | 324/158 D |
| 4,625,733 | A | 12/1986 | Säynäjäkangas | 128/687 |
| 4,638,436 | A | 1/1987 | Badger et al. | 364/414 |
| RE32,361 | E | 2/1987 | Duggan | 128/696 |
| 4,642,463 | A | 2/1987 | Thoms | |
| 4,651,741 | A | 3/1987 | Passafaro | 128/633 |
| 4,655,880 | A | 4/1987 | Liu | 204/1 T |
| 4,678,916 | A | 7/1987 | Thomson | 250/370 |
| 4,681,111 | A | 7/1987 | Silvian | 128/419 PT |
| 4,703,756 | A | 11/1987 | Gough et al. | 128/635 |
| 4,719,919 | A | 1/1988 | Marchosky et al. | 128/401 |
| 4,750,495 | A | 6/1988 | Moore et al. | 128/419 PG |
| 4,769,547 | A | 9/1988 | Uber, III | 250/374 |
| 4,793,825 | A | 12/1988 | Benjamin et al. | 128/419 |
| 4,796,641 | A | 1/1989 | Mills et al. | 128/748 |
| 4,804,847 | A | 2/1989 | Uber, III | 250/370 F |
| 4,846,191 | A | 7/1989 | Brockway et al. | 128/748 |
| 4,847,617 | A | 7/1989 | Silvian | 340/970.16 |
| 4,900,422 | A | 2/1990 | Bryan et al. | 204/401 |
| 4,913,153 | A | 4/1990 | Hagmann et al. | 128/653 |
| 4,919,141 | A | 4/1990 | Zier et al. | 128/635 |
| 4,935,345 | A | 6/1990 | Guilbeau et al. | 435/14 |
| 4,944,299 | A | 7/1990 | Silvian | 128/419 PG |
| 4,958,645 | A | 9/1990 | Cadell et al. | 128/903 |
| 4,961,422 | A | 10/1990 | Marchosky et al. | 128/399 |
| 4,970,391 | A | 11/1990 | Uber, III | 250/374 |
| 4,976,266 | A | 12/1990 | Huffman et al. | 128/659 |
| 4,989,601 | A | 2/1991 | Marchosky et al. | 128/399 |
| 5,008,546 | A | 4/1991 | Mazziotta et al. | 250/366 |
| 5,012,411 | A | 4/1991 | Policastro et al. | 364/413.06 |
| 5,074,318 | A | 12/1991 | Campbell et al. | 128/89.9 |
| 5,098,547 | A | 3/1992 | Bryan et al. | 204/401 |
| 5,109,850 | A | 5/1992 | Blanco et al. | 128/635 |
| 5,117,113 | A | 5/1992 | Thomson et al. | 250/370.07 |
| 5,117,824 | A | 6/1992 | Keimel et al. | 128/419 PG |
| 5,121,748 | A | 6/1992 | Ditz et al. | 128/631 |
| 5,126,937 | A | 6/1992 | Yamaguchi et al. | 364/413.11 |
| 5,127,404 | A | 7/1992 | Wyborny et al. | 128/419 P |
| 5,137,022 | A | 8/1992 | Henry | 128/419 PT |
| 5,148,404 | A | 9/1992 | Hilferink et al. | 362/2 |
| 5,159,262 | A | 10/1992 | Rumbaugh et al. | |
| 5,163,380 | A | 11/1992 | Duffy et al. | 119/15 |
| 5,166,073 | A | 11/1992 | Lefkowitz et al. | 436/57 |
| 5,186,172 | A | 2/1993 | Fiddian-Green | 128/632 |
| 5,193,538 | A | 3/1993 | Ekwall | 128/419 PT |
| 5,197,466 | A | 3/1993 | Marchosky et al. | 128/399 |
| 5,205,294 | A | 4/1993 | Flach et al. | 128/696 |
| 5,215,887 | A | 6/1993 | Saito | 435/14 |
| 5,264,843 | A | 11/1993 | Silvian | 340/870 |
| 5,309,085 | A | 5/1994 | Sohn | 324/71.5 |
| 5,314,450 | A | 5/1994 | Thompson | 607/32 |
| 5,318,023 | A | 6/1994 | Vari et al. | |
| 5,324,315 | A | 6/1994 | Grevious | 607/60 |
| 5,330,634 | A | 7/1994 | Wong et al. | 204/409 |
| 5,354,314 | A | 10/1994 | Hardy et al. | 128/653 |
| 5,354,319 | A | 10/1994 | Wyborny et al. | 607/32 |
| 5,355,880 | A | 10/1994 | Thomas et al. | 128/633 |
| 5,372,133 | A | 12/1994 | Hogen et al. | 128/631 |
| 5,377,676 | A | 1/1995 | Vari et al. | |
| 5,383,909 | A | 1/1995 | Keimel | 607/5 |
| 5,400,382 | A | 3/1995 | Welt et al. | 378/69 |
| 5,425,361 | A | 6/1995 | Fenzlein et al. | 128/635 |
| 5,431,171 | A | 7/1995 | Harrison et al. | 128/698 |
| 5,444,254 | A | 8/1995 | Thomson | 250/370.07 |
| 5,466,246 | A | 11/1995 | Silvian | 607/32 |
| 5,470,345 | A | 11/1995 | Hassler et al. | 607/36 |
| 5,476,488 | A | 12/1995 | Morgan et al. | 607/30 |
| 5,476,634 | A | 12/1995 | Bridges et al. | 422/22 |
| 5,477,050 | A | 12/1995 | Kronenberg et al. | 250/336.1 |
| 5,480,415 | A | 1/1996 | Cox et al. | 607/32 |
| 5,481,262 | A | 1/1996 | Urbas et al. | 340/870.17 |
| 5,497,772 | A | 3/1996 | Schulman et al. | 128/635 |
| 5,505,828 | A | 4/1996 | Wong et al. | 205/777.5 |
| 5,507,786 | A | 4/1996 | Morgan et al. | 607/27 |
| 5,517,313 | A | 5/1996 | Colvin, Jr. | 356/417 |
| 5,535,752 | A | 7/1996 | Halperin et al. | 128/670 |
| 5,538,005 | A | 7/1996 | Harrison et al. | 128/698 |
| 5,543,111 | A | 8/1996 | Bridges et al. | 422/22 |
| 5,545,187 | A | 8/1996 | Bergstrom et al. | 607/31 |
| 5,549,113 | A | 8/1996 | Halleck et al. | 128/633 |
| 5,549,654 | A | 8/1996 | Powell | 607/25 |
| 5,556,421 | A | 9/1996 | Prutchi et al. | 607/36 |
| 5,557,702 | A | 9/1996 | Yoshikawa et al. | 385/143 |
| 5,562,713 | A | 10/1996 | Silvian | 607/32 |
| 5,564,434 | A | 10/1996 | Halperin et al. | 128/675 |
| 5,571,148 | A | 11/1996 | Loeb et al. | 607/40 |
| 5,572,027 | A | 11/1996 | Tawil et al. | |
| 5,572,996 | A | 11/1996 | Doiron et al. | |
| 5,591,217 | A | 1/1997 | Barreras | 607/5 |
| 5,593,430 | A | 1/1997 | Renger | 607/9 |
| 5,596,199 | A | 1/1997 | McNulty et al. | |
| 5,606,163 | A | 2/1997 | Huston et al. | 250/337 |
| 5,609,820 | A | 3/1997 | Bridges et al. | 422/23 |
| 5,620,472 | A | 4/1997 | Rahbari | 128/903 |
| 5,620,475 | A | 4/1997 | Magnusson | 607/30 |
| 5,620,479 | A | 4/1997 | Diederich | 607/97 |
| 5,626,630 | A | 5/1997 | Markowitz et al. | 607/60 |
| 5,626,862 | A | 5/1997 | Brem et al. | 424/426 |
| 5,628,324 | A | 5/1997 | Sarbach | 128/670 |
| 5,630,413 | A | 5/1997 | Thomas et al. | 128/633 |
| 5,637,876 | A * | 6/1997 | Donahue et al. | 250/474.1 |
| 5,656,815 | A | 8/1997 | Justus et al. | 250/337 |
| 5,656,998 | A | 8/1997 | Fujiuchi et al. | 340/571 |
| 5,681,611 | A | 10/1997 | Yoshikawa et al. | 427/163.2 |
| 5,682,888 | A | 11/1997 | Olson et al. | 128/653.1 |
| 5,720,771 | A | 2/1998 | Snell | 607/60 |
| 5,731,957 | A | 3/1998 | Brennan | 361/728 |
| 5,732,704 | A | 3/1998 | Thurston et al. | 128/659 |
| 5,744,094 | A | 4/1998 | Castberg et al. | 422/24 |
| 5,744,804 | A | 4/1998 | Meijer et al. | 250/369 |
| 5,744,805 | A | 4/1998 | Raylman et al. | 250/370.01 |
| 5,759,199 | A | 6/1998 | Snell et al. | 607/60 |
| 5,787,144 | A | 7/1998 | Findlay | 378/69 |
| 5,791,344 | A | 8/1998 | Schulman et al. | 128/635 |
| 5,811,814 | A | 9/1998 | Leone et al. | 250/368 |
| 5,814,089 | A | 9/1998 | Stokes et al. | 607/32 |
| 5,833,603 | A | 11/1998 | Kovacs et al. | 600/317 |
| 5,840,148 | A | 11/1998 | Campbell et al. | 156/275.5 |
| 5,847,391 | A | 12/1998 | Sephton et al. | 250/336.1 |
| 5,855,203 | A | 1/1999 | Matter | 128/207.14 |
| 5,857,463 | A | 1/1999 | Thurston et al. | 128/659 |
| 5,879,375 | A | 3/1999 | Larson et al. | 607/30 |
| 5,891,179 | A | 4/1999 | Er et al. | 607/27 |
| 5,916,167 | A | 6/1999 | Kramer et al. | 600/436 |
| 5,918,110 | A | 6/1999 | Abraham-Fuchs et al. | 438/48 |
| 5,928,150 | A | 7/1999 | Call | 600/436 |
| 5,932,879 | A | 8/1999 | Raylman et al. | 250/370.06 |
| 5,939,453 | A | 8/1999 | Heller et al. | |
| 5,949,075 | A | 9/1999 | Kishi | 250/370.07 |
| 5,987,350 | A | 11/1999 | Thurston | 600/436 |
| 6,001,067 | A | 12/1999 | Shults et al. | 600/584 |
| 6,015,390 | A | 1/2000 | Krag | 600/549 |
| 6,025,137 | A | 2/2000 | Shyjan | |
| 6,031,454 | A | 2/2000 | Lovejoy et al. | |

| | | | | |
|---|---|---|---|---|
| D423,377 S | | 4/2000 | Atterbury et al. | D10/47 |
| 6,047,214 A | | 4/2000 | Mueller et al. | 607/61 |
| D424,453 S | | 5/2000 | Atterbury et al. | D10/47 |
| 6,070,096 A | | 5/2000 | Hayashi | |
| 6,076,009 A | | 6/2000 | Raylman et al. | 600/436 |
| 6,087,666 A | | 7/2000 | Huston et al. | 250/484.5 |
| 6,093,381 A | | 7/2000 | Triozzi et al. | 424/1.49 |
| 6,099,821 A | | 8/2000 | Rich et al. | 424/1.61 |
| 6,119,697 A | | 9/2000 | Engel et al. | |
| 6,132,681 A | * | 10/2000 | Faran et al. | 422/58 |
| 6,172,368 B1 | | 1/2001 | Tarr et al. | |
| 6,177,677 B1 | | 1/2001 | Alboresi et al. | 250/453.11 |
| 6,219,573 B1 | | 4/2001 | Pompei | |
| 6,239,724 B1 | | 5/2001 | Doron et al. | 340/870.28 |
| 6,240,312 B1 | | 5/2001 | Alfano et al. | 600/476 |
| 6,242,741 B1 | | 6/2001 | Miller et al. | 250/363.02 |
| 6,259,095 B1 | | 7/2001 | Bouton et al. | 250/336.1 |
| 6,272,373 B1 | | 8/2001 | Bouton | 600/436 |
| 6,274,159 B1 | | 8/2001 | Marotta et al. | |
| 6,295,680 B1 | | 10/2001 | Wahl et al. | 14/1 |
| 6,304,766 B1 | | 10/2001 | Colvin, Jr. | |
| 6,363,940 B1 | | 4/2002 | Krag | 128/899 |
| 6,398,710 B1 | | 6/2002 | Ishikawa et al. | 600/3 |
| 6,402,689 B1 | | 6/2002 | Scarantino et al. | |
| 6,444,475 B1 | | 9/2002 | Anderson, Jr. et al. | 436/161 |
| 6,614,025 B2 | | 9/2003 | Thomson et al. | |
| 6,650,930 B2 | | 11/2003 | Ding | |
| 6,746,465 B2 | | 6/2004 | Diederich et al. | |

FOREIGN PATENT DOCUMENTS

| | | | |
|---|---|---|---|
| DE | 3219558 | A1 | 1/1983 |
| DE | 4341903 | A1 | 6/1995 |
| EP | 0364045 | | 10/1989 |
| EP | 0420177 | A1 | 3/1991 |
| EP | 0471957 | A2 | 7/1991 |
| EP | 0537761 | A2 | 4/1993 |
| EP | 0245073 | B1 | 12/1993 |
| EP | 0386218 | B1 | 10/1996 |
| GB | 2 263 196 | | 7/1993 |
| JP | 63221278 | | 9/1988 |
| JP | 02147882 | | 6/1990 |
| JP | 07306269 | | 11/1995 |
| SU | 414900 | | 7/1976 |
| SU | 1603314 | A1 | 10/1990 |
| WO | WO 95/17809 | | 6/1995 |
| WO | WO 97/33513 | | 9/1997 |
| WO | WO 98/02209 | A2 | 1/1998 |
| WO | WO 98/43701 | | 8/1998 |
| WO | WO 98/05965 | | 12/1998 |
| WO | WO 98/58250 | | 12/1998 |
| WO | WO 99/48419 | | 9/1999 |
| WO | WO 99/58065 | | 11/1999 |
| WO | WO 99/63881 | | 12/1999 |
| WO | WO 00/29096 | | 5/2000 |
| WO | WO 00/18294 | | 6/2000 |
| WO | WO00/33065 | | 6/2000 |
| WO | WO 00/40299 | | 7/2000 |
| WO | WO 02/039917 | | 11/2000 |
| WO | WO 01/22874 | | 4/2001 |
| WO | WO 02/09775 | | 2/2002 |
| WO | WO 02/39918 | | 5/2002 |
| WO | WO 02/086449 | | 10/2002 |
| WO | WO 02/100485 | | 12/2002 |
| WO | WO 03/047694 | | 7/2003 |

OTHER PUBLICATIONS

Biotelemetrics, Inc., 6520 Contempo Lane, Boca Raton, Florida 33433, Tel: 407-394-0315. Biotelemetry Page, http://speed.nimh.nih.gov/telemetry/classx.html, Feb. 1997.

Data Sciences International, http://www.ispex.ca/companies/instrumentation/DataScInt.html, Profile web pages 1-2 and Instrumental Products 1-7, Copyright Ispex Exchange Inc., 2003; for examination purposes, applicant admits similar devices were available prior to earlier filing date of application.

Deutsch, S., "Fifteen-electrode time-multiplex eeg telemetry from ambulatory patients," *IEEE Transactions on Biomedical Engineering*, vol. BME-26, pp. 153-159 (1979).

Farrar IV, Harry et al., *Gamma-Ray Dose Mapping in Operational Candu Reactor Containment Areas Using MOS Dosimeters*, pp. 441-446, Reactor Dosimetry, ASTM, (1994).

Fernald, K., T. Cook, T. Miller, III, J. Paulos, "A microprocessor-based implantable telemetry systems," *Computer*, vol. 24, No. 7, pp. 23-30 (1991).

Fryer, T., H. Sndler, W. Freund, E. McCutcheon, E. Carlson, "A multichannel implantable telemetry system for flow, pressure, and ECG measurements," *Jour. of Applied Physiology*, vol. 39, pp. 318-326 (1973).

Holmstrom, N., P. Nilsson, J. Carlsten, S. Bowald, "Long-term in vivo experience of an electrochemical sensor using the potential step technique for measurement of mixed venous oxygen pressure," *Biosensors & Bioelectronics* 13, pp. 1287-1295 (1998).

Konigsberg Instruments, Inc., http://guide.labanimal.com/guide/companyd.jsp?b=3930, Lab Animal p. 1, Product Categories p. 1, Lab Animal Buyers Guide 2003 p. 1 and Animal Research Equipment pp. 1-12, Nature Publishing Group, 2003; for examination purposes, applicant admits similar devices were available prior to earlier filing date of application.

Lambrechts, M., Sansen, W., *Biosensors: Microelectrochemical Device*, NY, NY: IOP Publishing Ltd., pp. 206-208 (1992).

Lowe, S., et al., "p53 status and the efficacy of cancer therapy in vivo," *Sci.* , vol. 266, pp. 807-810 (1994)..

NASA Fact Sheet, Radiation Detector for Badges for Space Walkers, 3 sheets, (Oct. 2001).

Olthuis, W., Bergveld, P., "Simplified design of the coulometric sensor-actuator system by the application of a time-dependent actuator current," *Sensors and Actuators B*, vol. 7, pp. 479-483 (1992).

Pauley, Donald J., R. Martin, "A microminiature hybrid multichannel implantable biotelemetry system," *Biotelemetry Patient Monitoring*, vol. 8, pp. 163-172 (1981).

Pendower, J., *Spontaneous Disappearance of Gall-stones*, Medical Memoranda, British Medical Journal, pp. 492, 1964.

Thomson, I. et al., *Radiation Dosimetry with MOS Sensors*, Radiation Protection Dosimetry, Viol. 6, No. 1-4, Nuclear Technology Publishing, pp. 121-124, (1984).

Wayne, E. et al., *Treatment of Thyroid Disorders*, To-day's Drugs, British Medical Journal, pp. 493-496, Aug. 22, 1964.

Wouters, P., M. De Cooman, R. Puers, "A multi-purpose CMOS sensor interface for low-power applications," *IEEE Journal of Solid-State Circuits*, vol. 29, No. 8, pp. 952-956 (Aug. 1994).

Young, R. C., V. T. DeVita, "Cell cycle characteristics of human solid tumors in vivo," *Cell Tissue Kinetics* vol. 3, pp. 285-290 (1970).

Alecu et al., *Dose perturbations due to in vivo dosimetry with diodes* Radiotherapy and Oncology, pp. 289-291, vol. 42, (1997).

Jornet et al., *Calibration of semiconductor detectors for dose assessment in total body irradiation*, Radiotherapy and Oncology, pp. 247-251, vol. 38, (1996).

Loncol et al., "*Entrance and exit dose measurements with semiconductors and thermoluminescent dosemeters: a comparison of methods and in vivo results*", Radiotherapy and Oncology, pp. 179-187, vol. 41, (1996).

Halvorsen, H., *Dosimetric evaluation of a new design MOSFET in vivo dosimeter*, Med. Phys. 32 (1), Jan. 2005; pp. 110-117.

http://www.cirsinc.com/products/model_plasticwater.html, *Plastic Water™, Calibrate photon and electron beams with 0.5% of true water dose*, Computerized imaging Reference Systems, Inc., Dated Feb. 16, 2005, 1 sheet, © 2001.

Essers, M. et al., "In Vivo Dosimetry During External Photon Beam Radiotherapy", Int. J. Radiation Oncology Biol. Phys., vol. 43, No. 2, pp. 245-259, 1999.

Akabani, Gamal, *Absorbed Dose Calculations in Haversian Canals for Several Beta-Emitting Radionuclides*, Journal of Nuclear Medicine; 34:1361-1366, (1993).

Akin et al., *RF telemetry powering and control of hermetically sealed integrated sensors and actuators*, Proc. Solid-State Sensors & Actuators Workshop, Hilton Head, SC, pp. 145-148 (1990).
Almond et al. *AAPM's TG-51 protocol for clinical reference dosimetry of high-energy photon and electron beams*, Med. Phys. 26 (9), pp. 1847-1870, (Sep. 1999).
Barber et al., *Comparison of NaI(TI), CdTe, and HgI2 surgical probes: physical characterization*, Med. Phys., 18(3):373-381 (May-Jun. 1991).
Barthe, Jean, *Electronic dosimeters based on solid state detectors*, Nuclear Instruments and Methods in Physics Research B 184, pp. 158-189 (Jan. 2001).
Berthold et al., *Method for in-situ detection of tritium in water*, McDermott Technology Inc./RDTPA 99-03, pp. 1-9 (Sep. 19-22, 1999).
Blackstock et al., *Tumor retention of 5-fluorouracil following irradiation observed using 19F nuclear magnetic resonance spectroscopy*, Init J Radiat Oncol Biol Phys, 36(3):641-648 (Oct. 1, 1996).
Bojsen et al., *A portable external two-channel radiotelemetrical GM-detector unit, for measurements of radionuclide-tracers in vivo*, Int J Appl Radiat Isot, 25(4):161-166 (Apr. 1974).
Bojsen et al., *A radiotelemetrical measuring device, implantable on animals, for long term mersurements of radionuclide tracers*, Int J Appl Radiat Isot, 23(11):505-511 (Nov. 1972).
Brochure, *Be as smart as you can be with BMDS and Smart Alec™ your partners in intelligence*, Bio Medic Data Systems, Inc. (© 1999).
Brochure, *Come along for the incredible journey in the development of the IPTT-200*, Bio Medic Data Systems, Inc. (© 2000).
Butson, Martin J. et al., *A new radiotherapy surface dose detector: The MOSFET*, Med. Phys. 23 (5), pp. 655 658 (May 1996).
Cosofret et al., *Microfabricated sensor arrays sensitive to pH and K+ for ionic distribution measurements in the beating heart*, Analytical Chemistry, vol. 67, pp. 1647-1653 (1995).
Daghighian et al., *Intraoperative beta probe: a device for detecting tissue labeled with positron or electron emitting isotopes during surgery*, Med Phys, 21(1):153-157 (Jan. 1994).
Demidecki et al. *Considerations on the calibration of small thermoluminescent dosimeters used for measurement of beta particle absorbed doses in liquid environments*, Med. Phys. 20 (4), 1079-1087, Jul./Aug. 1993.
Dewhirst et al., *Soft-Tissue Sarcomas: MR Imaging and MR Spectroscopy for Prognosis and Therapy Monitoring*, Radiology, 174:847-853 (1990).
Dewhirst, "Concepts of oxygen transport at the microcirculatory level," *Seminars in Radiation Oncology*, vol. 8, 1998, pp. 143-150.
Dienes et al., *Radiation Effects in Solids, Interscience Monographs in Physics and Astronomy*, vol. II, Interscience Publishers, Inc., pp. 1-4; 56-85; 90-122 and 129-177 (© 1957).
Dimitrakopoulou et al., *Studies with Positron Emission Tomography After Systemic Administration of Fluorine-18-Uracil in Patients with Liver Metastases from Colorectal Carcinoma*, J Nucl Med, 34:1075-1081 (Jul. 1993).
Fernald, *A microprocessor-based system for the fast prototyping of implantable instruments for biomedical research applications*, Doctoral Dissertation, Elect. & Computer Eng., NC State Univ., (1992).
Fisher, DR, *Radiation dosimetry for radioimmunotherapy. An overview of current capabilities and limitations*, Cancer, 73(3 Suppl):905-911 (Feb. 1, 1994).
Gelezunas et al., *Silicon avalanche radiation detectors: the basis for a new ini vivo radiation detection probe*, Eur J Nucl Med, 8(10):421-424 (1983).
Gerweck, *Tumor pH: Implications for Treatment and Novel Drug Design*, 8 Seminars in Radiation Oncology, No. 5, pp. 176-182 (Jul. 1998).
Gilligan et al., *Evaluation of a subcutaneous glucose sensor out to 3 months in a dog model*, Diabetes Care, vol. 17, pp. 882-887 (1994).
Gladstone et al. *A miniature MOSFET radiation dosimeter probe*, Med. Phys. 21 (11), pp. 1721 1728, (Nov. 1994).
Gladstone et al. *Real-Time, In Vivo Measurement of Radiation Dose during Radioimmunotherapy in Mice Using a Miniature MOSFET Dosimeter Probe*, Radiation Research 141, pp. 330-335 (1995).
Grätz et al.; *Smart card for detection of alpha radiation Sensors and Actuators* 61 431-435 (1997).
Griffiths et al., *The OxyLite: a fibre-optic oxygen sensor*, British J. of Radiology, vol. 72 pp. 627-630 (1999).
Gschwend et al., *A general-purpose implantable multichannel telemetry system for physiological research*, Biotelemetry Patient Monitoring, vol. 6, pp. 107-117 (1979).
Hamburger et al, *Primary Bioassay of Human Tumor Stem Cells*, Science, 197:461-463 (1977).
Hassan et al., *A radiotelemetry pill for the measurement of ionizing radiation using a mercuric iodide detector*, Phys med Biol, 23(2):302-308 (Mar. 1978).
Heij et al., *Intraoperative search for neuroblastoma by MIBG and radioguided surgery with the gamma detector*, Med Pediatr Oncol, 28(3):171-174 (Mar. 1997).
Hines, *Advanced Biotelemetry Systems for Space Life Sciences: PH Telemetry*, Biotelementry XIII, Mar. 26-31, pp. 131-137 (1995).
Hoffman et al., *Intraoperative probes and imaging probes*, Eur Jnl Nucl Med, 26(8):913-935 (Aug. 1999).
Kastrissios et al., *Screening for Sources of Interindividual Pharmacokinetic Variability in Anticancer Drug Therapy: Utility of Population Analysis*, Cancer Investigation, 19(1):57-64 (Jan. 30, 2001).
Kern, D.H., *Tumor Chemosensitivity and Chemoresistance Assays*, Cancer 79(7):1447-1450 (1997).
Khouri et al., *An implantable semiconductor beta-radiation detector*, Am J Physiol, 232(1):H95-98 (Jan. 1977).
Kissel et al., *Noninvasive determination of the arterial input function of an anticancer drug from dynamic PET scans using the population approach*, Med Phys 26(4):609-615 (Apr. 1999).
Kolbert et al. *Implementation and Evaluation of Patient-Specific Three-Dimensional Internal Dosimetry*, Journal of Nuclear Medicine, vol. 38, No. 2, pp. 301-307, (Feb. 7, 1996).
Koutcher et al., *Potentiation of a Three Drug Chemotherapy Regimen by Radiation*, Cancer Res, 53:3518-3523 (1993).
Leichner, et al., *Patient-Specific Dosimetry of Indium-111- and Yttrium-90-Labeled Monoclonal antibody CC49*, Journal of Nuclear Medicine, vol. 38, No. 4, pp. 512-516, (Apr. 1997).
Liu, et al., *A Radionuclide Therapy Treatment Planning and Dose Estimation System*, The Journal of Nuclear Medicine, vol. 40, No. 7, pp. 1151-1153, (Jul. 1999).
Loeb et al., *Injectable microstimulator for functional electrical stimulation*, Med. & Biol. Eng. & Comput., vol. 29, pp. NS13-NS19 (1991).
Ma et al., in *Ionizing Radiation Effects in MOS Devices and Circuits*, John Wiley & Sons, pp. 35-46 (1989).
Mackay, *Bio-Medical Telemetry, Sensing and Transmitting Biological Information from Animals and Man*, Second edition. New York, NY: IEEE Press (1993).
Marzouk et al., *Electrodeposited Iridium Oxide pH Electrode for Measurement of Extracellular Myocardial Acidosis during Acute Ischemia*, Anal. Chem., vol. 70, pp. 5054-5061 (1998).
Mathur, V.K., *Ion storage dosimetry*, Nuclear Instruments and Methods in Physics Research B 184, pp. 190-206 (Jan. 2001).
Messenger et al., *The Effects of Radiation on Electronic Systems*, Van Nostrand Reinhold, pp. 332-349 (1992).
Mittal et al., *Evaluation of an Ingestible Telemetric Temperature Sensor for Deep Hyperthermia Applications*,: Int. J. Radiation Oncology Biol. Phys., vol. 21, pp. 1353-1361 (1991).
Mueller et al., *Feasibility of inductive powering of miniature low-power biotelemetry for use with microfabricated biomedical sensors*, Proc. Biotelemetry XIII, Williamsburg, VA, pp. 372-377 (Mar. 1995).
Nardin et al., *A multichannel neuromuscular microstimulator with bidirectional telemetry*, Proc. Int. Conf. on Solid-State Sensors and Actuators, Stockholm, Sweden, vol. 1, pp. 59-62 (Jun. 1995).
Oshima et al, *Development of Micro-Telemetering Multi-Sensor Capsule System with newly developed LSI for the clinical applications*, Transducers '87, The 4th International Conference on Solid-State Sensors and Actuators; pp. 163-166 (1987).
Piwnica-Worms et al., *Functional Imaging of Multidrug-resistant P-Glycoprotein with an Organotechnitium Complex*, Cancer Res, 53:977-984 (1993).

Presant et al., *Enhancement of Fluorouracil Uptake in Human Colorectal and Gastric Cancers by Interferon or by High-Dose Methotrexate: An In Vivo Human Study Using Noninvasive $^{19}F$-Magnetic Resonance Spectroscopy*, J Clin Oncol, 18:255-261 (2000) Jan. 4, 1999.

Present et al., *Human tumor fluorouracil trapping: clinical correlations of in vivo 19F nuclear magnetic resonance spectroscopy pharmacokinetics*, J Clin Oncol, 8(11):1868-1873 (Nov. 1990).

Puers et al., *A low power multi-channel sensor interface for use in digital telemetry*, Sensors and Actuators A, vols. 37-38, pp. 260-267 (1993).

Ranii, D., N&O Article, *Company's device aims to monitor disease from inside.*, Mar. 30, 2000.

Ranii, D., N&O Article, *Sicel seeks go-ahead for clinical trials*. Apr. 17, 2002.

Raylman et al., *Evaluation of ion-implanted-silicon detectors for use in intraoperative positron-sensitive probes*, Med Phys, 23(11):1889-1895 (Nov. 1996).

Shani, Gad *Radiation Dosimetry Instrumentation and Methods*, CRC Press, Boca Raton, Florida, 5 sheets including Table of Contents (1991).

Siegel et al., *MIRD Pamphlet No. 16: Techniques for Quantitative Radiopharmaceutical Biodistribution Data Acquisition and Analysis for Use in Human Radiation Dose Estimates*, Journal of Nuclear Medicine, 40:37S-61S, (1999).

Siegel et al., *The Importance of Patient-Specific Radiation Dose Calculations for the aministration of Radionuclides in Therapy*, Cellular and Molecular Biology 48 (5), pp. 451-459, (Mar. 1, 2002).

Small Business Innovation Research Program Phase One Grant Application entitled *An Implantable Multi-channel System for Monitoring Tumors*, submitted on or about Dec. 1996 to U.S. Public Health Service.

Small Business Innovation Research Program Phase One Grant Application entitled *An Implantable Multi-channel System for Monitoring Tumors*, resubmitted with revisions on or about Aug. 1997 to the National Institute of Health.

Small Business Innovation Research Program Phase One Grant Application entitled *An Implantable Multi-channel System for Monitoring Tumors*, resubmitted to the U.S. funding authority on or about Apr. 1998.

Soubra, M. et al., *Evaluation of a dual bias dual metal oxide-silicon semiconductor field effect transistor detector as radiation dosimeter*, Med. Phys. 21 (4), pp. 567-572 (Apr. 1994).

Stabin, M. G. *Internal Radiation Dosimetry*, Nuclear Medicine, Part Two, The Scientific Basis of Nuclear Medicine, pp. 316-333, (1996).

Stenson et al., *Effects of implantable biomaterials on radiation dosimetry*, Head Neck, vol. 19, No. 5 pp. 384-390 (Aug. 1997).

Stevens et al., *5-Flourouracil metabolism monitored in vivo by $^{19}F$ NMR*, Br J Cancer, 50:113-117 (1984).

Taylor et al., *The Forces in the Distal Femur and the Knee During Walking and Other Activities Measured by Telemetry*, J. of Anthroplasty, vol. 13, No. 4, pp. 428-437 (1998).

UCL Christian de Duve Institute of Cellular Pathology, Ludwig Institute for Cancer Research, URL www.lcp.ucl.ac.be/report95/licr95.html (1995).

Von Hoff et al., *Selection of Cancer Chemotherapy for a Patient by an In Vitro Assay Versus a Clinician*, JNCI 82:110-116 (1990) Oct. 25, 1989.

Watanabe et al., *A Preliminary Report on Continuous Recording of Salivary pH Using Telemetry in an Edentulous Patient*, Int'l J. Proshodontics, vol. 12, No. 4, pp. 313-317 (1999).

Webster, Editor, *Design of Cardiac Pacemakers*, IEEE Press, pp. 155-157 (1995).

Williams et al., *Multipurpose chip for physiological measurements*, IEEE International Symposium on Circuits and Systems, vol. 4, pp. 255-258, Proc. 1994.

Wolf et al., *Potential of microsensor-based feedback bioactuators for biophysical cancer treatment*, Biosensors & Bioelectronics, vol. 12, pp. 301-309 (1997).

Wolf et al., *19F-MRS studies of fluorinated drugs in humans*, Adv Drug Deliv Rev, 41(1):55-74 (Mar. 15, 2000).

Wolf et al., *Non-invasive 19F-NMRS of 5-fluorouracil in pharmacokinetics and pharmacodynamic studies*, NMR Biomed 11(7):380-387 (Nov. 1998).

Wolf et al., *Tumor trapping of 5-fluorouracil: In vivo $^{19}F$ NMR spectroscopic pharmacokinetics in tumor-bearing humans and rabbits*, Proc Natl Acad Sci USA, 87:492-496 (Jan. 1990).

Woolfenden et al., *Radiation detector probes for tumor localization using tumor-seeking radioactive tracers*, AJR Am J Roentgenol, 153(1):35-39 (Jul. 1989).

Yarnell et al., *Drug Assays on Organ Cultures of Biopsies from Human Tumours*, Br Med J 2:490-491 (1964).

Zanzonico et al., *The intraoperative gamma probe: basic principles and choices available*, Semin Nucl Med 30 (1):33-48 (Jan. 2000).

Zuckier et al., *Remotely Pollable Geiger-Muller Detector for Continuous Monitoring of Iodine-131 Therapy Patients*, J. of Nuclear Med., vol. 39, No. 9, pp. 1558-1562 (Sep. 1998).

National Aeronautics and Space Administration, "Extravehicular Activity Radiation Monitoring (EVARM)," Fact Sheet FS 2001-11-191-MSFC, abstract review, Oct. 2001.

Reece M.H. et al., "Semiconductor Mosfet Dosimetery," Health Physics Society Annual Meeting, 1988, pp. 1-14.

Shortt, Dr. Ken et al., "A New Direct Reading Extremity Dosimeter—How the ED-1 Sensor works," Healthy Physics Society Annual Meeting, Jul. 1994.

Soubra, M. et al., "Evaluation of a dual bias dual metal oxide-silicon semiconductor field effect transistor detector as radiation dosimeter," Am. Assoc. Phys. Med., vol. 21, No. 4, Apr. 1994, pp. 567-572.

Farrar IV, Harry et al., "Gamma-Ray Dose Mapping in Operational Candu Reactor Containment Areas Using MOS Dosimeters," pp. 441-446 "Reactor Dosimetry," ASTM, 1994.

Thomson, I. et al., "Radiation Dosimetry with MOS Sensors," Radiation Protection Dosimetry, vol. 6, No. 1-4, Nuclear Technology Publishing, 1984, pp. 121-124.

Moreno, D.J., Hughes, R.C.; Jenkins, M.W.; and Drumm, C.R.; A simple Ionizing Radiation Spectrometer/Dosimeter based on Radiation Sensing Field Effect Transistors (RadFETs), 1997 International Conference on Solid-State Sensors and Actuators, Chicago, pp. 1283-1286, Jun. 16-19 (1997).

NASA Fact Sheet, Extravehicular Activity Radiation Monitoring (EVARM), Product radiation detecetor badges for space walkers, pp. 1-3 Date unknown, believed to be before priority of application.

Reece, M.H. and Thomson, I.; "Semiconductor Mosfet Dosimetry", Thomson & Nielsen Electronics LTD. , Presented at Health Physics Society Annual Meeting pp. 1-14 (1988).

Shortt, Ken,; "A New Direct Reading Extremity Dosimeter", Presented at Health Physics Society Annual Meeting, Jul. (1994).

Tarr, N.G., Mackay, G.F., Shortt, K., and Thomson, I.; "A Floating Gate MOSFET Dosimeter Requiring No External Bias Supply", pp. 277-281, IEEE (1998).

PCT International Search Report, PCT/US 02/38111.

European Search Report for Application No. 02784637.7; date of mailing Sep. 15, 2006.

Peet, D.J. et al., *Evaluation of a MOSFET radiation sensor for the measurement of entrance surface dose in diagnostic radiology*, The British Journal of Radiology, 72, Jun. 1999, pp. 562-568.

Braichotte et al., *Clinical Pharmacokinetic Studies of Photofrin by Fluorescence Spectroscopy in the Oral Cavity, the Esophagus, and the Bronchi*, CANCER, vol. 75, No. 11, Jun. 1, 1995, pp. 2768-2778.

Cortese et al., *Clinical Application of a New Endoscopic Technique for Detection of In Situ Bronchial Carcinoma*, Mayo Clinic Proceedings, vol. 54, Oct. 1979, pp. 635-641.

Hansen, B., K. Aabo, J. Bojsen, *An implantable, Externally Powered Radiotelemetric System For Long-Term ECG And Heart-Rate Monitoring*, Biotelemetry Patient Monitoring, vol. 9., pp. 228-237 (1982).

Hirsch et al., *Early Detection of Lung Cancer: Clinical Perspective of Recent Advances in Biology and Radiology*, Clinical Cancer Research, vol. 7, Jan. 2001, pp. 5-22.

Kinsey et al., *Endoscopic System for Simultaneous Visual Examination and Electronic Detection of Fluorescence*, Review of Scientific Instruments, vol. 51, No. 10, Oct. 1980, pp. 1403-1406.

Kulapaditharom et al., *Performance Characteristics of Fluorescence Endoscope in Detection of Head and Neck Cancers*, Annals of Ontology, Rhinology & Laryngol, vol. 110 (1), Jan. 2001, pp. 45-52.

Ma et al., *The Photosensitizing Effect Of The Photoproduct Of Protoporphyrin IX*, J. Photochem Photobiol B, Jul. 2001, vol. 60 (2-3), pp. 108-113.

Mackay et al. *Gamma-Ray Dose Mapping in Operational Candu Reactor Containment Areas Using MOS Dosimeters*, pp. 441-446, Reactor Dosimetry, ASTM, 1994.

Mayinger et al., *Endoscopic Fluorescence Spectroscopy in the Upper GI Tract for the Detection of GI Cancer: Initial Experience*, The American Journal of Gastroenterology, vol. 96, No. 9, Sep. 2001, pp. 2616-2621.

Mayinger et al., *Light-induced Autofluorescence Spectroscopy for the Endoscopic Detection of Esophageal Cancer*, Gastrointestinal Endoscopy, vol. 54, No. 2, Aug. 2001, pp. 195-201.

Miller et al., *Clinical Molecular Imaging*, J Amer Coll Radiol 2004, 1, pp. 4-23.

Mycek et al., *Colonic Polyp Differentiation Using Time-Resolved Autofluorescence Spectroscopy*, Gastrointest. Endosc., Oct. 1998, No. 48 (4), pp. 390-394.

PCT International Search Report, International Application No. PCT/US01/47373 dated Aug. 6, 2002.

PCT International Search Report, International Application No. PCT/US02/12855 dated Dec. 16, 2002.

Rollins et al., *Potential New Endoscopic Techniques For The Earlier Diagnosis Of Pre-Malignancy*, Best Pract. Res. Clin. Gastroenterol, Apr. 2001, vol. 15 (2), pp. 227-247.

Schantz et al, *In Vivo Native Cellular Fluorescence And Histological Characteristics Of Head And Neck Cancer*, Clin. Cancer Res., May 1998, vol. 4 (5), pp. 1177-1182.

Stepp et al., *Fluorescence Endoscopy Of Gastrointestinal Diseases: Basic Principles, Techniques, And Clinical Experience*, Endoscopy, May 1998, vol. 30 (4), pp. 379-386.

Sweeney et al., *Visualization The Kinetics Of Tumor-Cell Clearance In Living Animals*, PNAS, vol. 96, No. 21, pp. 12044-12049, Oct. 12, 1999.

Van Den Bergh,, H., *On the Evolution of Some Endoscopic Light Delivery Systems for Photodynamic Therapy*, Endoscopy, May 1998, pp. 392-407.

Yang et al., *Visualization Gene Expression By Whole-Body Fluorescence Imaging*, PNAS, vol. 97, No. 22, pp. 12278-12282, Oct. 24, 2000.

Zonios, et al., *Diffuse Reflectance Spectroscopy Of Human Adenomatous Colon Polyps In Vivo*, Applied Optics, Nov. 1999, vol. 1; 38 (31), pp. 6628-6637.

http://www.thomson-elec.com/lineararray.htm, *Linear Array, Linear 5ive MOSFET Array*, Thomson/Nielsen Monitoring radiation in this world and beyond . . . , Dated Feb. 16, 2005, 5 sheets.

http://www.thomson-elec.com/buildupcaps.html, *Build-up Caps, Hemispherical Build-up Caps*, Thomson/Nielsen Monitoring radiation in this world and beyond . . . , © 2004, 1 sheet.

* cited by examiner

99

One Dose™ Dosimetry Form

150

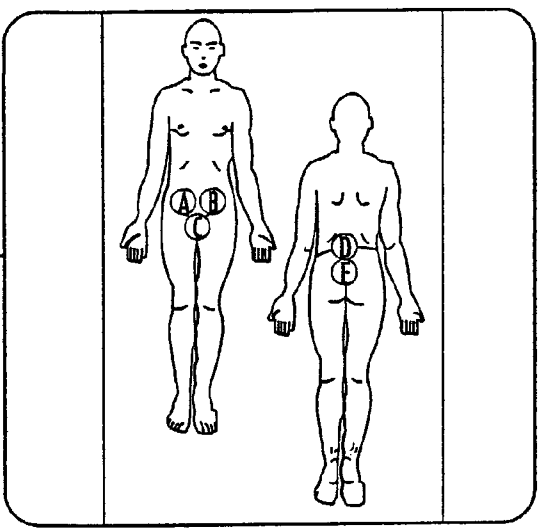

Dosimetry Plan

Date: ______

Patient: ______

Doctor: ______

Notes:

152

Mesurement Data:

Date: ______

Therapist: ______

154

156

158

| | | | | | |
|---|---|---|---|---|---|
| A | Pre | Post | Field: ______ ☐ Entrance ☐ Exit | Target Dose (cGy) | Measured Dose (cGy) |
| B | Pre | Post | Field: ______ ☐ Entrance ☐ Exit | Target Dose (cGy) | Measured Dose (cGy) |
| C | Pre | Post | Field: ______ ☐ Entrance ☐ Exit | Target Dose (cGy) | Measured Dose (cGy) |
| D | Pre | Post | Field: ______ ☐ Entrance ☐ Exit | Target Dose (cGy) | Measured Dose (cGy) |
| E | Pre | Post | Field: ______ ☐ Entrance ☐ Exit | Target Dose (cGy) | Measured Dose (cGy) |
| F | Pre | Post | Field: ______ ☐ Entrance ☐ Exit | Target Dose (cGy) | Measured Dose (cGy) |

158

© Sicel Technologies, Inc. 2001

FIG. 4.

SINGLE-USE EXTERNAL DOSIMETERS FOR USE IN RADIATION THERAPIES

RELATED APPLICATION

This application claims priority from U.S. Provisional Patent Application Ser. No. 60/334,580 entitled Disposable Single-Use External Dosimeters for Use in Radiation Therapies, filed Nov. 30, 2001, the contents of which are hereby incorporated herein by reference.

FIELD OF THE INVENTION

The present invention generally relates to the assessment or quantitative evaluation of the amount of radiation delivered to a patient undergoing radiation therapy.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

BACKGROUND OF THE INVENTION

Conventionally, radiation therapy is delivered over a successive series of radiation treatment sessions. High-energy photons and/or electrons are carefully directed and/or focused from an ex vivo radiation source so that they travel into a targeted treatment area in a patient's body. The size, shape, and position of the treatment area (typically where a tumor is or was) as well as its anatomical location in the body and its proximity to sensitive normal tissues are considered when generating a particular patient's treatment plan. That is, the treatment is planned so as to deliver a suitably high dose of radiation to the tumor or targeted tissue while minimizing the dose to nearby sensitive tissue that typically cannot be completely avoided. Directing radiation into non-affected regions may produce undesired side effects particularly as it relates to tissue that may be sensitive to certain dosages of radiation. Unfortunately, even when the patient plan is carefully constructed to account for the location of the cancerous tissue and the sensitive non-affected regions, even small errors in set-up due to beam angle or patient position during delivery of the radiation therapy can inadvertently misdirect radiation into those regions or can influence the dose amount that is actually received by the targeted tissue. Further, the demand for radiation treatment equipment is typically relatively high and this demand may limit the set-up time allowed or allocated in the treatment room between patients.

In the past, implantable devices for oncology applications have been proposed to evaluate the radiation dose amount received in vivo at the tumor site. See e.g., U.S. Pat. No. 6,402,689 to Scarantino et al., the contents of which are hereby incorporated by reference herein. Measuring the radiation at the tumor site in vivo can provide improved estimates of doses received. However, for certain tumor types or situations, a skin-mounted or external surface radiation dosimeter may be desirable and sufficient for clinical purposes.

Conventional external or skin-mounted radiation dosimeter systems use semiconductor circuitry and lead wires that power/operate the dosimeters. These types of dosimeters are available from Scandatronics and/or IBA ("Ion Beam Applications") having an international headquarters location in Belgium. While these radiation dosimeter systems may provide radiation dose estimations, they can, unfortunately, be relatively expensive. Further, these types of dosimeters are used for a plurality of patients potentially raising sterility or cleanliness problems between patients. Conventional dosimeter systems may also require substantial technician time before and during the radiation session. For example, conventional dosimeter systems need to be calibrated before the radiation session may begin. In addition, the lead wires can be cumbersome to connect to the patients and may require excessive set-up time as the technician has to connect the lead wires to run from the patient to the monitoring system and then store the lead wire bundle between patient treatment sessions. Therefore, technicians do not always take the time to use this type of system, and no confirmation estimate of the actual radiation delivered is obtained.

Other radiation sensors include thermo-luminescent detectors (TLD's). However, while TLD detectors do not require wires during operation, they are analyzed using a spectrophotometer (that may be located in an offsite laboratory) and are not conducive to real-time readings.

In view of the foregoing there remains a need for improved economical and easy to use radiation dosimeters.

OBJECTS AND SUMMARY OF THE INVENTION

It is therefore an object of the present invention to provide a cost-effective surface mount radiation dosimeter that can be used to evaluate the radiation dose delivered to a patient undergoing radiation therapy.

It is a further object of the present invention to provide economic methods and devices that can reduce labor set-up time in the radiation treatment chamber over conventional evaluation methods and devices.

It is an additional object of the present invention to provide a memory storage device on the patch to record the dose history of the patch. This memory storage device may be queried at any time in order to obtain a record of the dose applied to the patch. Other information, such as patient identification, time, date, hospital, therapist, state of the device, dosed/undosed and calibration data may be stored in the memory storage device.

It is an additional object of the present invention to provide an economic method of determining the amount of radiation delivered to an oncology patient in situ.

These and other objects can be satisfied by the present invention by a disposable, single-use skin mounted radiation dosimeter that has a self-contained package that is small, adhesively attachable to the skin of the patient, and operates in a relatively easy to operate and read manner without requiring the use of lead wires.

Certain embodiments of the present invention are directed to methods for monitoring radiation doses administered to patients undergoing radiation treatments. The methods include the steps of: (a) releasably securing at least one single-use dosimeter sensor patch onto the skin of the patient such that the patch is self-contained and devoid of leads extending therefrom; (b) administering radiation to the patient in a first treatment session; (c) contacting the sensor patch with a dose-reader device after the administering step to obtain data associated with a change in an operational parameter in the dosimeter sensor patch; and (d) determining the radiation dose received by the patient during the administering step based on the change in the operational parameter.

In some embodiments, the sensor patch may be pre-dosed and/or calibrated before the sensor patch is secured to the patient. The obtained data may be stored in an electronic storage device provided on the sensor patch itself. The storage device may be, for example, an EEPROM. Other information, such as the patient's name, the doctor's name, the test date and the like, may also be stored in the storage device provided on the sensor patch. Alternatively, the data can be stored on a computer readable memory integrated on a physical record sheet that can be placed in the patient's file.

Other embodiments are directed to systems for monitoring radiation administered to a patient during a therapeutic treatment. The system comprises: (a) at least one disposable single-use dosimeter patch, the patch comprising a body holding a circuit with at least one MOSFET and an external reader contact region thereon, the MOSFET(s) having an associated threshold voltage that changes when exposed to radiation, the body comprising opposing upper and lower primary surfaces; and (b) an external portable dose-reader being configured to make electrical contact with the patch by physically engaging with the contact region on the patch to obtain voltage threshold data corresponding to the dose amount of radiation exposure it is exposed to in use. During operation, the patch has a perimeter that is devoid of outwardly external lead wires.

In some embodiments, the patch includes a conformable resilient body. The lower primary surface may include a medical grade adhesive and the sensor patch may be pressed on to secure the sensor patch to the patient. In other embodiments, an adhesive coverlay is applied over the sensor patch to secure the sensor to the patient. A portion or all of the sensor patch may be adapted to be inserted into the dose-reader to transmit the dose data and the dose-reader may similarly be adapted to receive a portion or all of the sensor patch. Insertion of the sensor patch into the reader electrically couples the sensor to the reader and allows the reader to receive the radiation dose data from the sensor patch. The sensor patch may also include an electronic storage device in electrical communication with the sensor. The sensor patch may then be pre-dosed and/or calibrated before the radiation session. Data may be downloaded from the memory of the sensor patch to a remote computer and/or a computer application using the electrical coupling of the sensor patch and the dose-reader.

In certain embodiments, the at least one dosimeter patch is a plurality of discrete sensor patches and the reader is configured to serially contact with each respective sensor patch to obtain the threshold voltage value associated therewith.

A sheet of sensor patches may be pre-dosed and/or calibrated simultaneously or individually before the sensor patches are secured to the patient. The calibration and/or pre-dosing may be performed at the original equipment manufacturer (OEM) or at the actual test site. The sheet of sensor patches may include about 30 to about 100 sensors. The sensors may also be provided in a high density array of sensors where so many sensors are provided in a certain area of the high density array, for example, multiple sensors may be provided per square inch or per 3 by 3 inch regions of the high density array.

Still other embodiments are directed to sets of disposable single-use radiation dosimeter patches. The sets comprise a plurality of discrete disposable single-use dosimeter patches, each patch comprises a conformable body holding a circuit with an operational electronic component that changes a parameter in a detectable predictable manner when exposed to radiation, the body comprising opposing upper and lower primary surfaces and the dosimeter patch, in use and positioned on the patient, is devoid of externally hanging lead wires.

The operational electronic component may be a radiation sensitive biased MOSFET or MOSFETs (such as MOSFET pairs) and the detectable operational parameter that changes can be the MOSFET threshold voltage(s). Furthermore, a medical grade adhesive may be supplied on the lower primary surface of the sensor body such that the sensor may be adhered to the patient's skin. In certain embodiments, an adhesive coverlay may be provide over the body of the sensor to secure the sensor to the patients skin.

Another embodiment is directed to a computer program product for evaluating a radiation dose delivered to a patient. The computer program product comprises a computer readable storage medium having computer readable program code embodied in the medium. The computer-readable program code comprises: (a) computer readable program code for receiving pre-irradiation threshold voltage data associated with a plurality of disposable sensor patches; (b) computer readable program code for accepting data from a reader configured to electrically serially contact each of the plurality of disposable sensors for a short time; and (c) computer readable program code for determining the voltage threshold shift of the disposable sensor patches after radiation to determine the radiation exposure.

In still further embodiments of the present invention, a dose-reader may be adapted to receive a sensor patch in a sensor port. The sensor patch is also adapted to be inserted in the sensor port. The dose-reader can be a pocket or palm sized portable device. The dose-reader may also include a communications port, for example, a universal serial port (USB), RS 232 and the like, for downloading obtained data to a computer application or remote computer. The dose-reader functionality may be incorporated into a personal digital assistant (PDA) or other pervasive computer device.

In further embodiments the sensor patch may be configured to communicate with the dose-reader wirelessly. For example, the sensor patch and the dose-reader may both be equipped with an radio frequency (RF) interface so that information may be shared between the two devices.

The foregoing and other objects and aspects of the present invention are explained in detail in the specification set forth below.

BRIEF DESCRIPTION OF THE FIGURES

FIG. 4 illustrates an exemplary patient information form according to embodiments of the present invention.

DESCRIPTION OF EMBODIMENTS OF THE INVENTION

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, certain components, features, or layers may be exaggerated for clarity. In the block diagrams or flow charts, broken lines indicate optional operations, or features unless stated otherwise.

Figure 1:
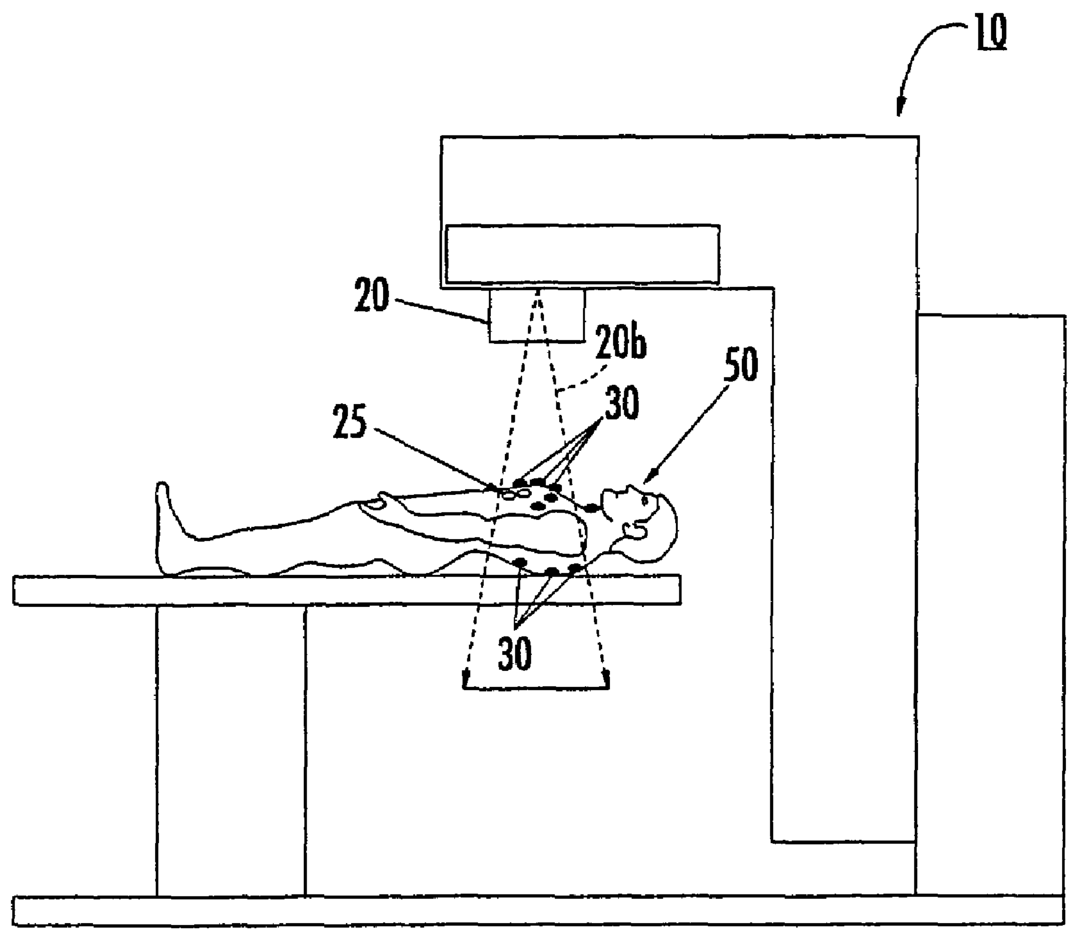
FIG. 1 is a schematic illustration of a patient undergoing radiation treatment according to embodiments of the present invention.

FIG. 1 illustrates an example of a radiation system 10 with a radiation beam source 20 directed at a patient 50 having a tumor site. The patient 50 can be positioned so as to be aligned and stationary with respect to the beam 20*b* (illustrated by the diverging dotted lines) during the treatment. As such, the patient 50 can be arranged in any desired position depending on the direction of the beam, the location of the tumor, and the type of radiation therapy system employed. As shown, the patient is reclined, substantially flat and face up on a table so that the beam 20*b* is directed into the targeted tumor site in the body as the patient undergoes radiation therapy in a treatment session. Typically, the patient will undergo a plurality of successive treatment sessions over a treatment period. Each treatment session may be planned to administer radiation doses of between about 1-2 Gray (100-200 cGy) with an overall treatment limit of about 35-80 Gray.

To help monitor or estimate the amount of radiation that is delivered to the patient during a treatment session, at least one disposable single-use dosimeter sensor patch 30 can be positioned externally on the skin of the patient 50. As used herein, "single-use" is used to refer to a use for a single patient during a treatment session. The sensor patch 30 may be episodically worn or continuously worn. It will be understood that a treatment session may include an active radiotherapy administration during a single treatment session or serially spaced apart treatment sessions. The treatment session may have a duration of minutes, hours, days and the like. Furthermore, a calibration dose obtained before the sensor patch 30 is positioned on a patient is not to be considered the "single-use."

As shown in FIG. 1, a plurality of sensor patches 30 are located both on the front and back of the patient 50. The sensor patches 30 are configured to change an operational parameter in a predictable manner that correlates to radiation dose it receives, as will be discussed further below. The sensor patch 30 can be configured so as to be self-contained and discrete and devoid of dangling lead wires extending to a remote power source or operating system during use and in position on the patient. As such, a reader, for example, reader 75 (FIGS. 6 and 7), can be configured to obtain the data from the sensor patch 30 by, for example, electrically contacting with each sensor patch 30 of interest.

As used herein, the reference number "75" will be used to refer generally to a reader device according to embodiments of the present invention. Particular embodiments of a reader device 75 may be referred to using the reference number 75 and one or more primes attached thereto. For example, particular embodiments of the reader device may be denoted 75' or 75". This convention may similarly be used with respect to other features of the present invention. For example, the reference number "30'" will be used to refer to particular embodiments of a sensor patch herein. It will be understood that features discussed with respect to any embodiment of the present invention may be incorporated into other embodiments of the present invention even if these features are not discussed specifically with reference to each individual embodiment.

Figure 2:
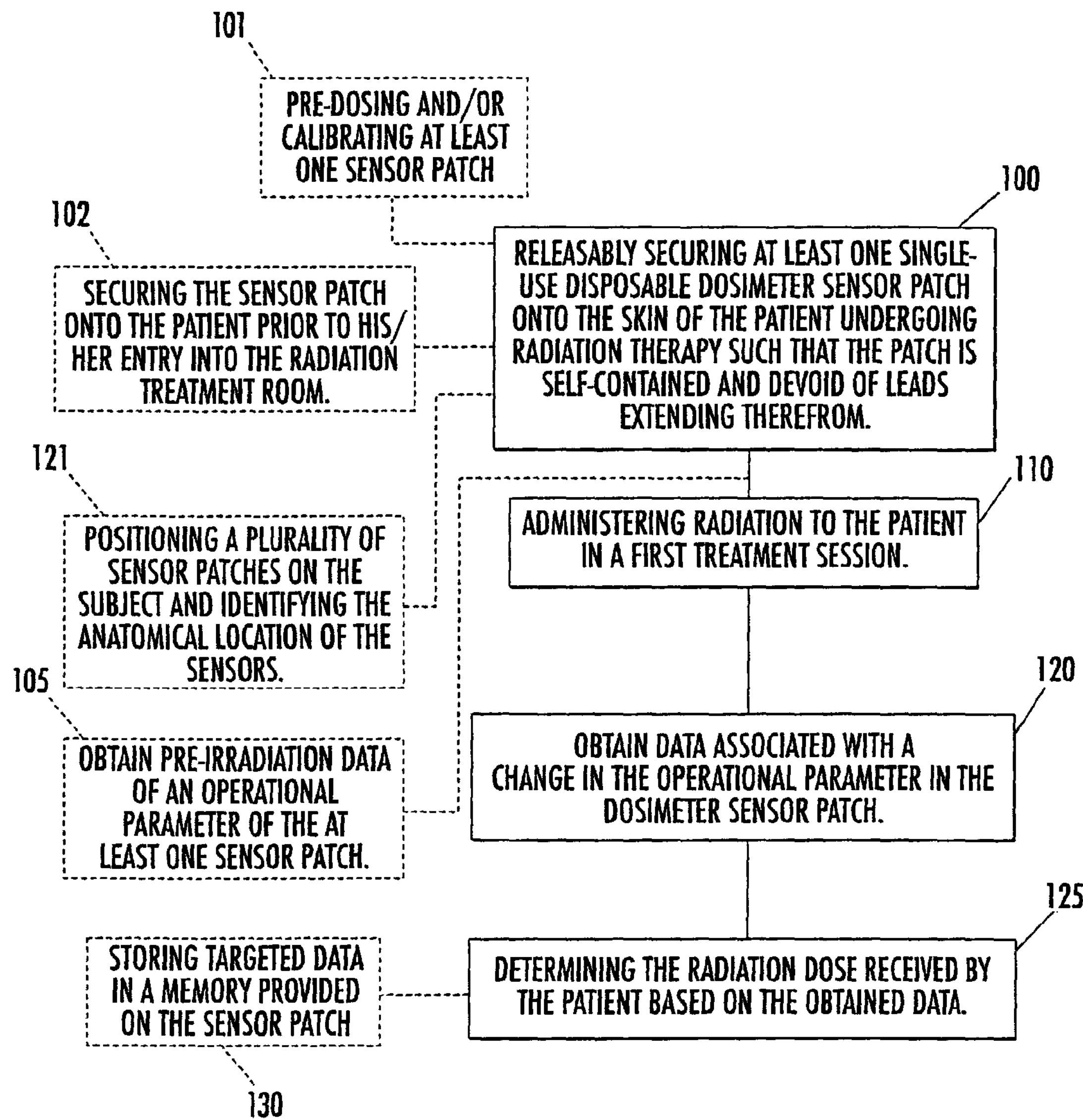
FIG. 2 is a block diagram of operations for monitoring patients undergoing radiation treatments according to embodiments of the present invention.

Referring to FIG. 2, operations that can be carried out to monitor the radiation dose that is delivered to a patient undergoing radiation therapy are illustrated. At least one single-use disposable dosimeter sensor patch can be releasably secured to the skin of the patient (block 100). In certain embodiments, the sensor patch may be calibrated and/or pre-dosed before being attached to the patient (block 101). The calibration and/or pre-dosing of the sensor patch may be done on an individual patch basis or many sensor patches may be calibrated and/or pre-dosed in batches simultaneously as discussed further below. In certain embodiments, the patch(es) can be conveniently attached to the patient in operation-ready condition before the patient enters the radiation treatment room or chamber (block 102) to limit or reduce the set-up time required or the "down-time" of the equipment or the treatment room. In other words, the sensor patch or patches may be secured to the patient prior to his/her entry into the radiation treatment room. A pre-irradiation or pre-dose measurement or reading of data associated with an operational parameter of the sensor patch(es) 30 can be obtained prior to initiation of the radiation treatment (block 105). The data can be obtained in situ, with the sensor patch(es) 30 in position on the patient. Alternatively, the pre-dose data can be established prior to positioning the sensor patch(es) onto the subject as discussed above and the data then transferred to the reader or associated controller and/or computer at a desired time.

In certain embodiments of the sensor patch(es), the post-radiation reading can be taken when the patient leaves the treatment room to evaluate the dose delivered during the treatment session to limit the amount of room-use time. The sensor patches 30 can be removed from the patient and then read by a handheld portable or a bench top reader. In other embodiments, the reading can be obtained while the sensor patches 30 remain on the patient. In certain particular embodiments, the reading may be able to be obtained in situ during the treatment session (without removing the sensor patch(es) from the patient) to provide real-time feedback to the clinician estimating whether the desired dose is being administered to the patient. In certain embodiments, the temperature of the sensor patch (such as at a location adjacent the circuitry) or of the subject (skin or core body) can also be ascertained or obtained and taken into account when calculating the radiation dose. In any event the dose reading can be obtained without requiring external powering or externally applied biasing of the sensor patches 30 during the radiation treatment.

In certain embodiments, a plurality of discrete sensor patches 30 can be positioned to cover a region on the skin that is in the radiation beam path so as to reside over the tumor site. In particular embodiments, one or more sensor patches 30 can also be positioned in radiation sensitive areas of the body to confirm stray radiation is not unduly transmitted thereto. FIG. 2 illustrates that a sensor patch can be located at the neck over the thyroid when the tumor site is over the chest region. As such, sensitive regions include, but are not limited to, the thyroid, the spine, the heart, the lungs, the brain, and the like. In any event, referring again to FIG. 1, radiation is administered to the patient in a first treatment session (block 110). Data associated with a change in an operational parameter in the dosimeter sensor patch circuitry may be obtained from the sensor patch using a reader device (block 120) after administering the radiation to the patient (block 110). In certain embodiments, a sensor patch may be removed from the patient and inserted into the reader device to transfer the data from the sensor patch. In further embodiments, the reader device may contact the sensor patch as discussed further below. The radiation dose received by the patient can be determined based on the obtained data (block 125). The obtained data as well as other information may be stored in a memory device included on the sensor patch as described further below (block 130).

The sensor patch does not require lead wires extending from a remote power source or computer system to operate. Instead, the sensor patch 30 is configured to be a discrete patch (or a patch array of sensors) that can transmit or relay data upon contact with and/or insertion into a reader device 75 and may store data in an electronic memory device included on the sensor patch. In certain embodiments, the sensor patch 30 may be configured to communicate wirelessly with the reader 75. The radiation dose received by the sensor patch 30 can be determined and used to estimate the dose received by the patient during the radiation therapy session based on the data obtained by the reader. The reader itself can be a handheld portable unit that may or may not include wires to connect with a remote controller or computer as will be discussed further below. In any event, the operations can be carried out for each or a selected radiation treatment session. If the operations are repeated for each treatment session, a cumulative amount of delivered radiation can be estimated/confirmed to allow a clinician to evaluate whether additional treatments are desired.

Figure 3A:
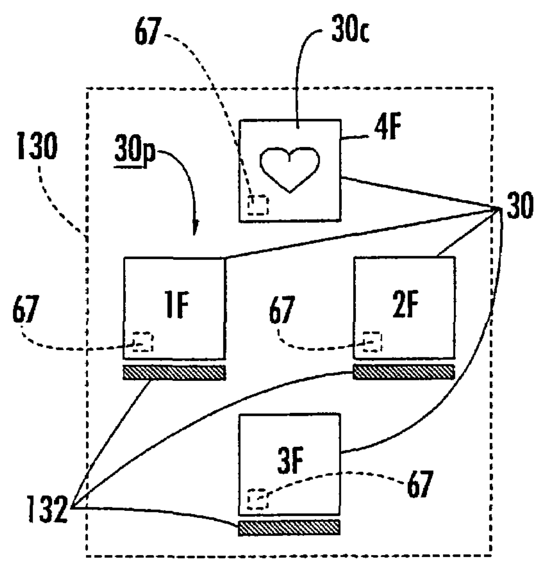
FIGS. 3A and 3B are illustrations of sets of disposable dosimeter patches according to embodiments of the present invention.
Figure 15A:
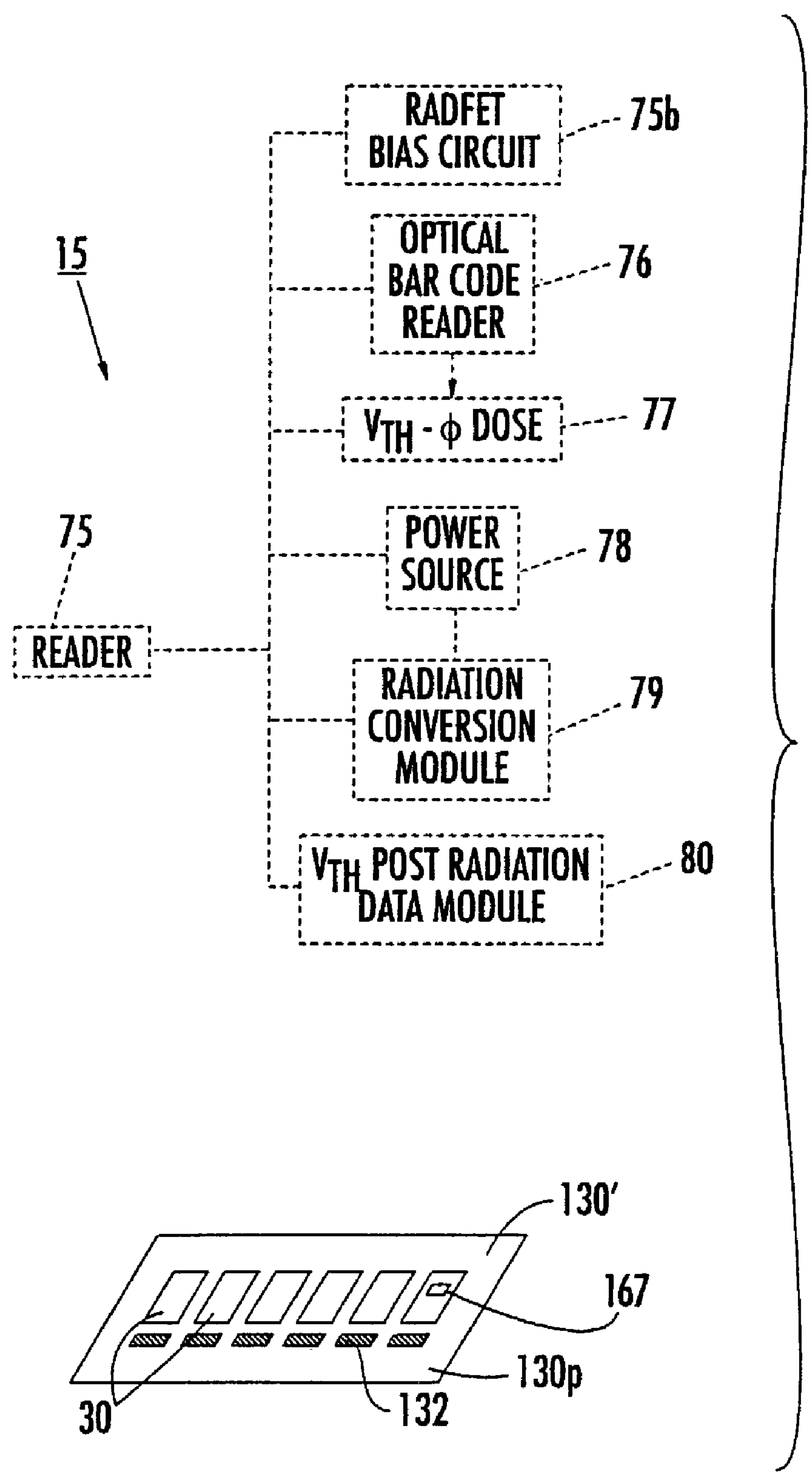
FIG. 15A is a schematic of a system or computer program product for estimating radiation based on data taken from a point contact-reader data acquisition system according to embodiments of the present invention.

FIG. 3A illustrates that the sensor patches 30 can be provided in a kit or set 130 including a plurality of sensors 30*p*. The plurality of sensors 30*p* may be configured in sufficient numbers or types for a single patient or so as to be able to supply sensors across a plurality of patients. In certain embodiments, a strip of six sensor patches 30 can be packaged together as a set 130' as shown in FIG. 15A. It is contemplated that, depending on the treatment type, the treatment location, the tumor site, and the like, different numbers of sensor patches 30 may be used for different patients. Thus, if the sensor kit 130 is sized for a single patient, the kit may include from about 2 to about 10 or more sensor patches 30 that can be selectively chosen for use by the clinician. Each sensor patch 30 can be sterilized and sealed in a sterile package or the kit 130 itself can be sized and configured to hold a plurality of the sensor patches 30*p* in a sterile package that, once opened, can be either used or discarded. Similarly, if the sensor kit 130 is sized for multi-patient use, then larger quantities may be packaged individually, or in sets within the multi-patient package, together. The sterilization can be performed by heat or chemical exposure, such as by ethylene oxide sterilization. In certain embodiments, sterilization and/or sterile packaging may not be required.

As is also shown in FIG. 3A, each sensor patch 30 can be packaged with pre-irradiation characterizing data 132. This data 132 can be included in optically or electronically readable formats such as in bar code format for the reader to be able to read without having the clinician enter the information into a controller/computer. In certain embodiments, the data 132 may be included in a memory storage device 67, for example, an electrically programmable memory such as an electrically erasable read only programmable memory (EEPROM), provided on each sensor patch 30*p* as discussed further below. The memory storage device 67 may include information such as patient identification, time, date, hospital, therapist, state of the device, dosed/undosed sensor data and calibration data. The memory storage device 67 may further be used to store bias parameters and/or information with respect to measurement methodology for each individual patch 30.

Each sensor patch 30 can have an individual calibration coefficient, dose data or characterizing data label located on the sensor patch 30 or as a corresponding label held with the package or kit 130. In other embodiments, each sensor patch 30 produced in a common production run (off of the same wafer or chip) with substantially similar characterizing data may be packaged together and a single calibration characterizing data or label 132 can be included with the set 130 or sets or production run. In certain embodiments, the calibration related characterizing data can include the pre-irradiation threshold voltage value of a metal-oxide semiconductor field-effect transistor(s) (MOSFET(s)) that is measured at an OEM and provided in or with the sensor patch set 130.

In certain embodiments, identifying indicia may be disposed on the sensor patches 30 to allow a clinician to easily visually identify and/or account for the sensors used. For example, FIG. 3A illustrates three discrete sensor patches labeled as 1F, 2F, and 3F as well as a sensor with a pictorial representation of a heart 4F (other visual images can also be used such as a yellow caution sign, other anatomical symbols, and the like). The heart or caution sensor patch 30*s* can be positioned in a radiation sensitive area to detect the amount of radiation delivered to that area. Typically, the radiation beam is adjusted to reduce the radiation exposure to sensitive areas and a caution-sensitive sensor patch 30*s* (or patches) can indicate whether adjustments need to be made to reduce the detected exposure for each or selected treatment sessions. The sensor patches 30*s* used for sensitive detection may be configured with increased sensitivity for enhanced dose resolution capability for measuring small, residual, or stray doses of radiation (such as those located over critical organs which are not in the treatment volume). For example, for "normal" single use sensors may be configured to operate over a range of between about 50-500 cGy; the "high sensitivity" sensor might be configured to operate from about 1-50 cGy. In particular embodiments, the circuit 30*c* (FIG. 9A) for the high sensitivity sensor 30*s* includes at least one radiation-sensitive field-effect transistor (RADFET) that can be configured to produce a larger threshold voltage shift for a given amount of received or absorbed dose relative to the sensors 30 positioned in the window of the targeted treatment volume. The larger voltage shift may increase dose resolution and possibly dose repeatability.

In addition, single-use dosimeters can be optimized to work over a much lower dose range than multiple use dosimeters. Since the typical per day fraction for radiation therapy is about 200 cGy, the dosimeter sensor 30 can be optimized for accuracy and repeatability over this dose range. A 50-500 cGy operating range should meet performance goals while providing adequate flexibility for varying treatment plans. A multiple-session fraction dosimeter sensor 30 may require a much larger dose range that depends on the number of fractions over which the sensor will operate. As used herein, "disposable" means that the sensor patch is not reusable and can be disposed of or placed in the patient's records.

Figure 3B:
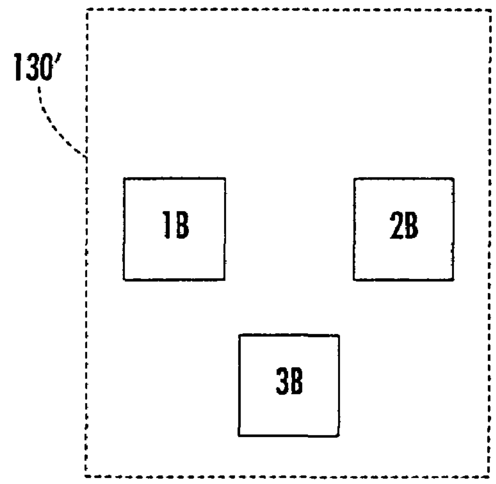

As shown in FIG. 3A, the indicia can include an alphanumeric identifier such as the letter "F" located to be externally visible on the sensor patches 30. The letter "F" can represent that the sensors are placed on a first side or front of the patient. FIG. 3B illustrates that a second set of sensors 130' can be supplied, these sensor patches 30 can be labeled with different indicia, such as 1B, 2B, 3B and the like, representing that they are located at a different location relative to the first set (such as a second side or back of the patient). Using data from opposing outer surfaces can allow an interpolated radiation dose amount to be established for the internal tumor site.

It will be understood that the indicia described above, namely "F" and "B", are provided herein for exemplary purposes only and that indicia according to embodiments of the present invention are not limited by the examples provided. Any label, mark, color or the like may be used that would serve to distinguish one patch or set of patches from another patch or set of patches without departing from the teachings of the present invention. For example, instead of "F" and "B", the first set of patches 130 may be blue and the second set of patches 130' may be red. Furthermore, the indicia may be, for example, on the sensor patch itself or on an adhesive covering placed on or over the sensor patch without departing from the teachings of the present invention.

Figure 3C:
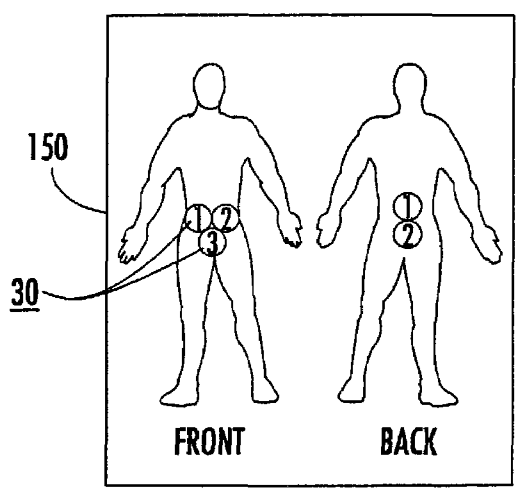
FIG. 3C is an anatomical map of sensor location according to embodiments of the present invention.

FIG. 3C illustrates a patient anatomical map 150 that can be used to identify where each of the sensor patches 30 are placed on the body of the patient. The map 150 may be stored in the patient chart or file. For each treatment session for which dose monitoring is desired, the clinician can allocate the same sensor patch identifier ("A", "1F", etc . . . ) to the same location. The map 150 and/or indicia on the sensor patches 30 can, in turn, help the clinician consistently identify whether a particular location may have undue or deficient exposure. For example, if sensor patch F1 indicates a low radiation exposure, while F3 indicates a relatively high exposure, and the two are positioned in the targeted beam region, either one or both of the sensor patches 30 is not functioning properly, or the radiation beam may need adjustment. Using substantially the same sensor patch position for successive treatment sessions may allow cumulative radiation dose data to be obtained and correlated to provide a more reliable indication of dose. The clinician may also draw markings on the patient's skin to help align the sensor patches 30 in relation thereto over the different treatments sessions.

In certain embodiments, the discrete sensor patches 30 can be arranged to reside on a common substrate or to be attached to each other so as to define known or constant distances therebetween (not shown). The sensor patches 30 may be configured to be at the body temperature of the patient during use or at room temperature, or temperatures in between. In certain embodiments, to establish a calculated dose amount, a temperature reading may be obtained, assumed, or estimated. In certain particular embodiments, the temperature may impact the operational change if substantially different from that upon which the calibration data is established.

In certain embodiments, a first set-up pre-dose verification protocol can be carried out to deliver a first radiation dose and a first radiation dose value can be obtained for at least one selected patch to confirm that the radiation beam focus location is correct or suitable (or whether a sensitive area is receiving radiation). In addition, the system can be configured to map a dose gradient by correlating the determined radiation dose values at each patch location to the anatomical location on the subject of each patch.

FIG. 4 illustrates an exemplary patient dosimetry form 99, which may be, for example, a paper sheet or computer printable document. The form 99 can contain an anatomical map 150 as discussed above with respect to FIG. 3C. Sicel Technologies, Inc. asserts copyright protection for the form illustrated in FIG. 4 and has no objection to reproduction of the patent document, as it appears in the Patent and Trademark Office patent file or records, but reserves all other rights whatsoever.

As discussed above, the map 150 may be used to identify and/or memorialize for the patient record where each of the sensor patches 30 are placed on the body of the patient during use. An anatomical map 150 can be used to record the specifics of each radiation session and may be placed in each patient's chart or file to assist the doctor and/or clinician. Patients being treated on an ongoing basis may have multiple dosimetry forms 99 in their chart and/or file corresponding to each treatment session. As noted above, for each treatment session, the clinician can, as desired, allocate the same sensor patch identifier to the same location aided by the map 150. As further illustrated in FIG. 4, the dosimetry form 99 may further include a dosimetry plan portion 152, a measurement data portion 154 and a sensor patch record portion 156.

The dosimetry plan portion 152 may include the patient's name, the date or dates the patient is scheduled for the treatment, the patient's doctor, and any information that may be specific to the patient or the patient's treatment. The measurement data portion 154 may include information such as the date of the treatment and the therapist administering the treatment on that date. The sensor patch record portion 156 may include labeled sections 158 (A, B, . . . ) giving each patient a discrete identifier which may correspond to sensor patch locations (A, B, . . . ) with the identifiers indicated on the anatomical map 150. The sensor patch record portion 156 may further include dosing data, for example, target and measured doses as illustrated in FIG. 4. The sensor patch record portion 156 may further include the actual sensor patch used on the patient in each of the labeled sections 158. As shown, the form 99 can include two separate storage regions, namely a pre and post dose use storage region. In addition, the form 99 can also allow a clinician to indicate whether the sensor patch was held in the entrance and/or exit field.

In certain embodiments, the sensor patch 30 may contain a storage or memory device 67 (FIGS. 3A, 9B), the storage or memory device on the sensor patches may be accessed to determine dosing information etc. if this information fails to be recorded, is misplaced or requires verification. Furthermore, the memory device 67 included on the sensor patch 30 may further include the data recorded in the map portion 150, the dosimetry plan portion 152 and the measurement data portion 154 of the dosimetry form 99. Accordingly, the memory device 67 on the sensor patch 30 may serve as an electronic dosimetry patient record form. It will be understood that the dosimetry form 99 of FIG. 4 is provided for exemplary purposes only and that the present invention may provide data and/or hold sensor patches in alternate manners without departing from the teachings of the present invention.

Figure 5A:
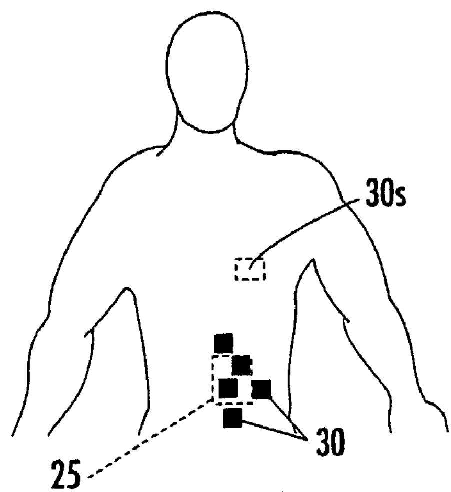
FIGS. 5A and 5B are schematic illustrations of sensor placement on a patient according to embodiments of the present invention.
Figure 5B:
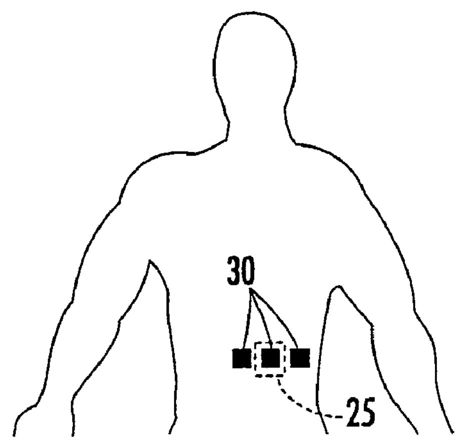

FIG. 5A illustrates the use of five primary sensor patches 30 positioned over the targeted treatment region (on the front side of the patient) and one sensor patch 30*s* positioned over the heart. FIG. 5B illustrates three primary sensors 30 located over the back surface proximate the area corresponding to the underlying tumor site 25.

Figure 6:
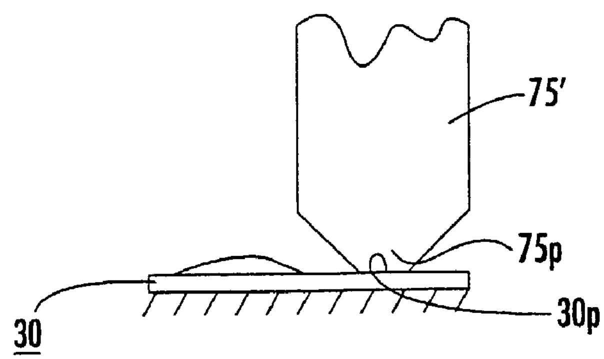
FIG. 6 is a schematic illustration of embodiments of a reader contacting the sensor to obtain the radiation dosage data according to embodiments of the present invention.

FIG. 6 illustrates a reader or data acquisition device 75' according to embodiments of the present invention, in point contact with the underlying sensor patch 30 in order to detect the amount of radiation that the sensor patch 30 was exposed to during (or after) the treatment session. In certain embodiments, as discussed above, the sensor patch(es) 30 can be secured to a patient's chart or dosimetry form 150 and read after removal from the patient. The reader 75' illustrated in FIG. 6 may be configured to contact a portion of an electrical circuit on the sensor patch 30 that includes a device that has an operating characteristic or parameter that changes upon exposure to radiation in a predictable manner to allow radiation doses to be determined. The reader 75' can be configured with a probe 75*p* that is configured to electrically contact an electrically conductive probe region on the sensor patch 30 so as to obtain a reading in a "short" time of under about 30 seconds, and typically in less than about 5-10 seconds, for each of the sensor patches 30.

Figure 7:
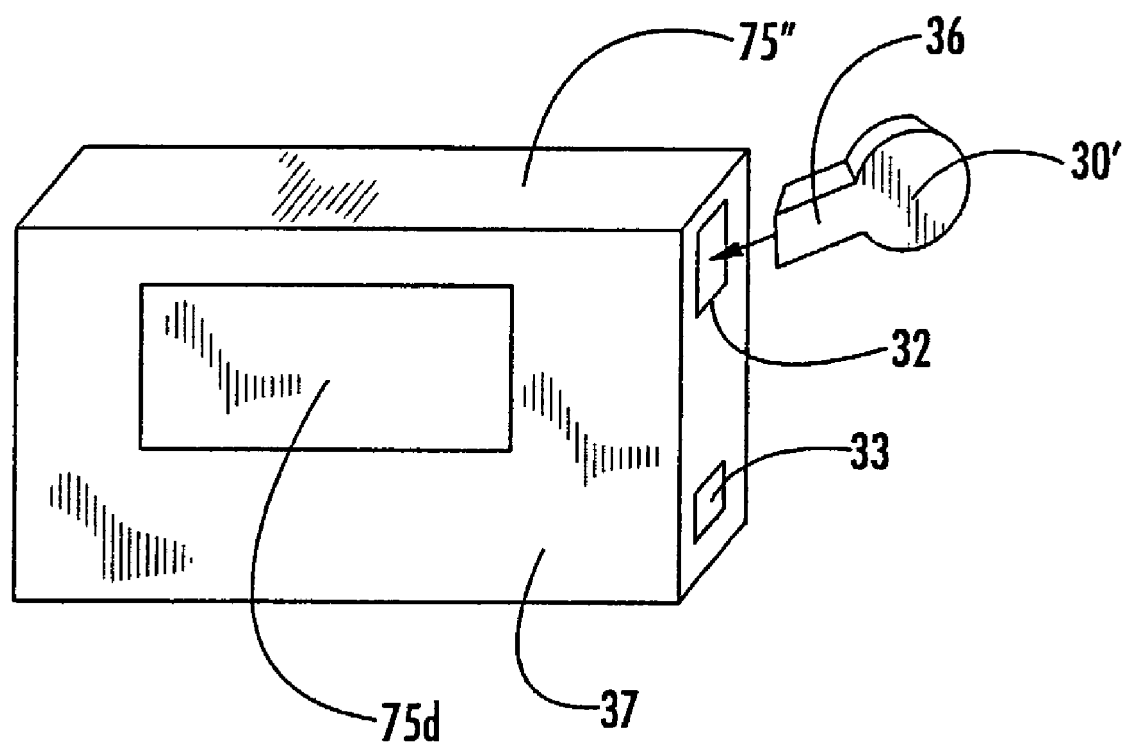
FIG. 7 is a schematic illustration of further embodiments of a reader receiving the sensor in a sensor port to obtain the radiation dosage data according to embodiments of the present invention.

Referring now to FIG. 7 a sensor patch 30' disposed in a reader or data acquisition device 75" according to further embodiments of the present invention. Sensor patches 30' according to embodiments of the present invention may be adapted to be inserted into the reader 75". Similarly, the reader 75" is adapted to receive the sensor patch 30'. As shown, the sensor patch 30' is formed to include a tab portion 36 that at least a portion of is sufficiently rigid to sustain its shape for proper electrical coupling when inserted into a port 32 in the reader device 75". As illustrated in FIG. 7, the reader 75" may include a sensor port 32 and the sensor patch 30' may be inserted into the port 32 in the reader 75" in order to detect the amount of radiation that the sensor patch 30' was exposed to. The port 32 can read the sensor patch 30 as it is held in selected orientations in the port 32. The port 32 may be configured similar to conventional devices that read, for example, glucose strip sensors and the like. The port 32 illustrated in FIG. 7 may contain one or more electrical contacts configured to contact one or more electrical contacts on the sensor patch 30' to electrically connect the reader 75" to an electrical circuit on the sensor patch 30'. The electrical circuit on the sensor patch 30' includes a radiation-sensitive component that has an operating characteristic or parameter that changes upon exposure to radiation in a predictable manner to allow radiation doses to be determined. As before, the reader 75" may obtain a reading in under about 30 seconds, and typically in less than about 5-10 seconds, for each of the sensor patches 30.

Figure 15B:
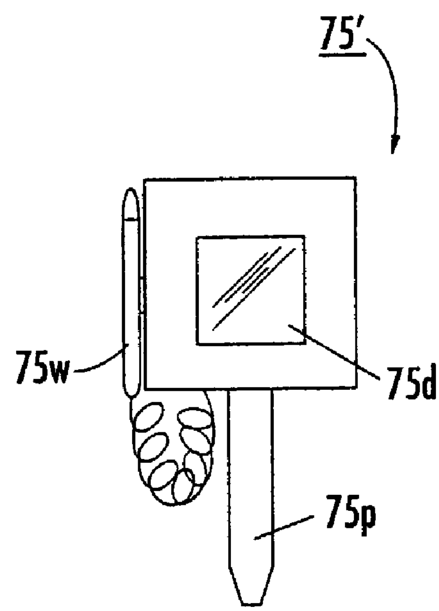
FIG. 15B is a block diagram illustrating a reader device according to embodiments of the present invention.

The reader device 75" can be held in a portable housing 37. It may be pocket sized and battery powered. In certain embodiments, the reader device 75 may be rechargeable. As shown in FIGS. 7, 15A and 15B, the reader 75 may include a display portion 75*d*, for example, a liquid crystal display (LCD), to provide an interface to depict data to the doctor and/or technician.

The function of the reader device 75 may be incorporated into any portable device adapted to receive a sensor patch 30 in, for example, a sensor port 32. For example, the reader 75 functionality/circuitry could be disposed in a personal digital assistant (PDA) that is adapted to include a radiation sensor port 32. The reader 75 may further include a remote computer port 33. The port 33 may be, for example, RS 232, infrared data association (IrDA) or universal serial bus (USB), and may be used to download radiation and/or other selected data from the sensor patch 30 to a computer application or remote computer. In some embodiments, the sensor patch 30 and the reader device 75 may both be equipped with an RF interface and information may be shared between them wirelessly.

In certain embodiments, as noted above, the sensor patch 30 includes a storage or memory device 67. In these embodiments, the reader 75 may be configured to obtain data stored in the memory device 67 of the sensor patch 30 using, for example, electrical contacts on the reader 75 and the patch 30, to transfer the data stored in the memory device 67 of the sensor patch 30. This data obtained from the sensor patch memory device 67 may, for example, be stored locally on the reader 75 or be downloaded to an application on, for example, a remote computer using a port 33 provided in the reader 75. The memory device 67 on the sensor patch 30 may serve as a permanent record of the radiation dose and may contain a real time clock such that the obtained data may include a time and date stamp.

Figure 8A:
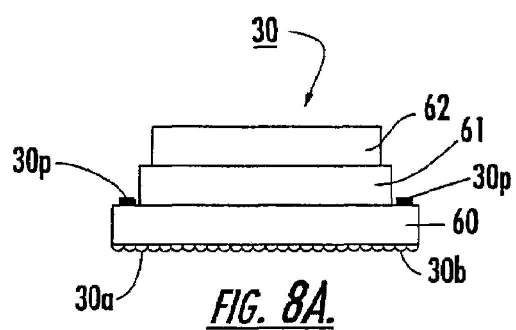
FIG. 8A is a greatly enlarged side view of a disposable radiation dosimeter according to embodiments of the present invention.

FIG. 8A illustrates exemplary embodiments of a sensor patch 30. As shown, the sensor patch 30 includes a substrate layer 60, a circuit layer 61, and an upper layer 62 that may be defined by a coating, film, or coverlay material. The substrate layer 60 can be selected such that it is resilient, compliant, or substantially conformable to the skin of the patient. Examples of suitable substrate layer materials include, but are not limited to, Kapton, neoprene, polymers, co-polymers, blends and derivatives thereof, and the like. The underside or bottom of the sensor patch 30*b* may include a releasable adhesive 30*a* so as to be able to attach to the skin of the patient. The adhesive 30*a* can be a medical grade releasable adhesive to allow the sensor patch 30 to be secured to the skin during the treatment session and then easily removed without harming the skin. The adhesive 30*a* can be applied to portions, or all, of the bottom surface of the substrate layer 60. In certain embodiments, the underside of the sensor patch 30*b* may be free of the adhesive. In these embodiments, an adhesive coverlay 30*cl* (FIG. 9C) may be placed over the body of the sensor patch 30 to secure the sensor patch 30 to the patient. The adhesive coverlay 30*cl* may be sized to extend beyond the outer perimeter of the sensor substrate 60. The adhesive may be on a portion or all of the underside of the coverlay 30*cl*.

In other embodiments, the sensor patch(es) 30 is configured as a discrete, low profile, compact non-invasive and minimally obtrusive device that conforms to the skin of the patient. The sensor patch(es) may be less from about 0.25 to about 1.5 inches long and wide and have a thin thickness of from about 1 to about 5 mm or less. As such, the sensor patches 30 can, in certain particular embodiments, be secured to the patient and allowed to reside thereon for a plurality or all of the successive treatments. For example, the sensor patches 30 can be configured to reside on the patient in its desired position for a 1-4 week, and typically about a 1-2 week period. In this manner, the same sensor patches 30 can be used to track cumulative doses (as well as the dose at each treatment session). An adhesive may be applied in a quantity and type so as to be sufficiently strong to withstand normal life functions (showers, etc.) during this time. Of course, selected ones of the sensor patches 30 can also be replaced as desired over the course of treatment as needed or desired.

In certain embodiments of the present invention, it may be important to attach the sensor patch 30 to the patient so that it makes and retains snug contact with the patient's skin. Air gaps between the sensor 30 and the patient's skin may cause complications with respect to obtaining the estimated dosage data. As illustrated in FIGS. 9D and 9E, some embodiments of the present invention include the placement of an overlay material 30*fl* over the sensor patch 30 to, for example, simulate placement of the sensor patch 30 beneath the patient's skin. This type of simulation may help to focus a narrow portion of the radiation beam in proximity to the sensor patch 30 and, therefore, increase the reliability of radiation measurement. Radiation measurement using the sensor subsurface electronics may be optimal at from about 0.5 to about 3 cm beneath the patient's skin, but typically is from about 1 to about 1.5 cm beneath the patient's skin. Accordingly, the overlay material 30*fl* may be from about 0.5 to about 3 cm thick to simulate subsurface depth measurement conditions. The presence of this overlay material 30*fl* may decrease the influence of air gaps between the sensor 30 and the patient's skin.

The overlay material 30*fl* may be, for example, a resilient flubber like or flexible material that will conform to the skin such as an elastomeric or the like. As illustrated in FIG. 9D, the overlay material 30*fl* may be placed between the adhesive coverlay 30*cl* and the sensor patch 30 such that the adhesive coverlay 30*cl* adheres the sensor patch 30 and the overlay material 30*fl* to the patient's skin. As illustrated in FIG. 9E, the overlay material 30*fl* may be placed over the adhesive coverlay 30*cl* and the sensor patch 30. In certain embodiments, the overlay material may have adhesive properties such that the overlay 30*fl* may be adhered to the patient's skin. The overlay material 30*fl* may also be integrated with the sensor patch 30 without departing from the teachings of the present invention.

Still referring to FIG. 8A, the sensor circuit layer 61 can be attached to, and/or formed on, the underlying substrate layer 60. The upper layer 62 can be configured as a moisture inhibitor or barrier layer that can be applied over all, or selected portions of, the underlying circuit layer 61. It is noted that, as shown, the thickness of the layers 60-62 are exaggerated for clarity and shown as the same relative thickness, however the thickness of the layers may vary. In certain embodiments, the sensor patch 30 is configured as a low profile, thin device that, when viewed from the side, is substantially planar.

Figure 8B:
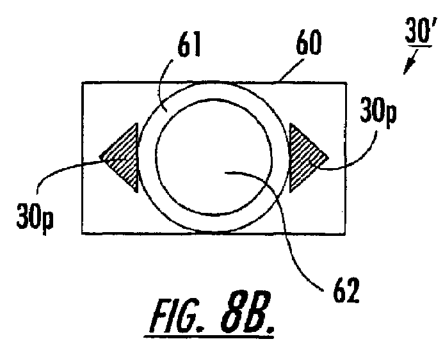
FIG. 8B is a top view of the dosimeter shown in FIG. 8A.

FIG. 8B is a top view of embodiments of a sensor patch 30. As shown, in certain embodiments, the circuit may layer include two conductive probe contacting regions 30*p*. During data readings/acquisitions, the probe contacting regions 30*p* are configured to provide the connections between the operating circuitry on the circuit layer 61 and the external reader. The probe contacting region(s) 30*p* can be directly accessible or covered with a protective upper layer 62. If directly accessible, during operation, the reader 75 can merely press against, contact or clip to the sensor patch 30 to contact the exposed surface of the conductive probe region 30*p* to obtain the reading. If covered by an upper layer 62 that is a protective coating or other non-conductive insulator material, the clinician may need to form an opening into the coating or upper layer over the region 30*p* so as to be able to penetrate into the sensor patch 30' a certain depth to make electrical contact between the probe region 30*p* and the probe of the reader 75*p*.

Figure 8C:
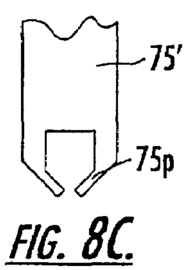
FIG. 8C is a partial cutaway view of a probe head for a reader according to embodiments of the present invention.

FIG. 8C illustrates a probe portion 75*p* of the reader 75' of FIG. 6. As illustrated, the probe portion 75*p* may be configured so that the probe 75*p* includes, for example, conductive calipers, pinchers, or other piercing means, that can penetrate to make electrical contact with the probe contacting region 30*p* of the sensor patch.

Figure 9A:
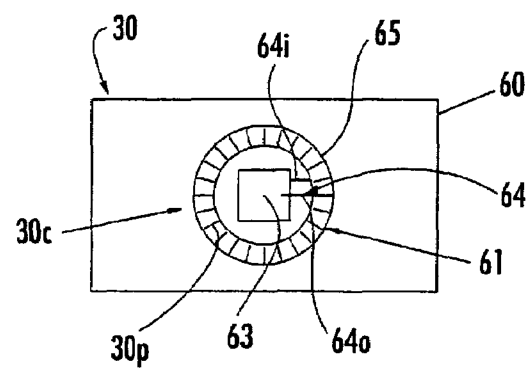
FIG. 9A is a schematic of embodiments of a sensor patch with a circuit thereon according to embodiments of the present invention.

FIG. 9A illustrates a top view of embodiments of a circuit layer 61. As shown, the circuit layer 61 includes the radiation sensitive operative sensor patch circuitry 30*c* that is self-contained and devoid of outwardly extending or hanging lead wires that connects to an operational member. The sensor patch circuitry 30*c* includes a radiation sensitive device 63 that exhibits a detectable operational change when exposed to radiation. In certain embodiments, the radiation sensitive device 63 is a miniaturized semiconductor component such as a MOSFET. Suitable MOSFETs include RADFETs available from NMRC of Cork, Ireland. In certain embodiments, the MOSFET may be sized and configured to be about 1-2 mm in width and length. The circuitry 30*c* also includes at least one conductive lead or trace 64 extending from the radiation sensitive device 63 to the conductive probe contacting region 30*p*. In the embodiment shown, the conductive probe contacting region 30*p* is an annular ring. As also shown there are two traces 64*i*, 64*o* that connect the device 63 to the ring 30*p*. The traces or leads 64' may be formed, placed, or deposited onto the substrate layer 60 in any suitable manner including, but not limited to, applying conductive ink or paint or metal spray deposition on the surface thereof in a suitable metallic pattern, or using wires. As desired, an upper layer 62 such as described above (such as epoxy) may be formed over the circuit layer 61 (or even the entire sensor patch). The sensor patch 30 may include integrated Electro Static Discharge (ESD) protection, the reader 75 may include ESD protection components, or the user/operator may use ESD straps and the like during readings.

In particular embodiments, the sensor patch 30 and circuit 30*c* can be configured with two or more MOSFETS. In embodiments configured to have two MOSFETS, one may be positioned over the other on opposing sides of the substrate in face-to-face alignment to inhibit orientation influence of the substrate. (not shown). Additionally, other materials, e.g., certain epoxies, can be used to both encapsulate the MOSFETs and provide further scattering influence to facilitate isotropic response of the MOSFETs. In addition, there are well known influences of radiation backscatter from the surface of patients on whom surface-mounted dosimeters are used. The backscatter effect can be taken into account when calculating an entrance or exit dose or sufficient build-up may be provided on the top of the dosimeter to promote the equilibration of scattered electrons. See, *Cancer, Principles and Practice of Oncology,* 3d edition, ed. V T DeVita, S. Hellman, and S A Rosenberg (JB Lippincott Co., Phila., 1989), the contents of which are hereby incorporated by reference as if recited in full herein.

Figure 9B:
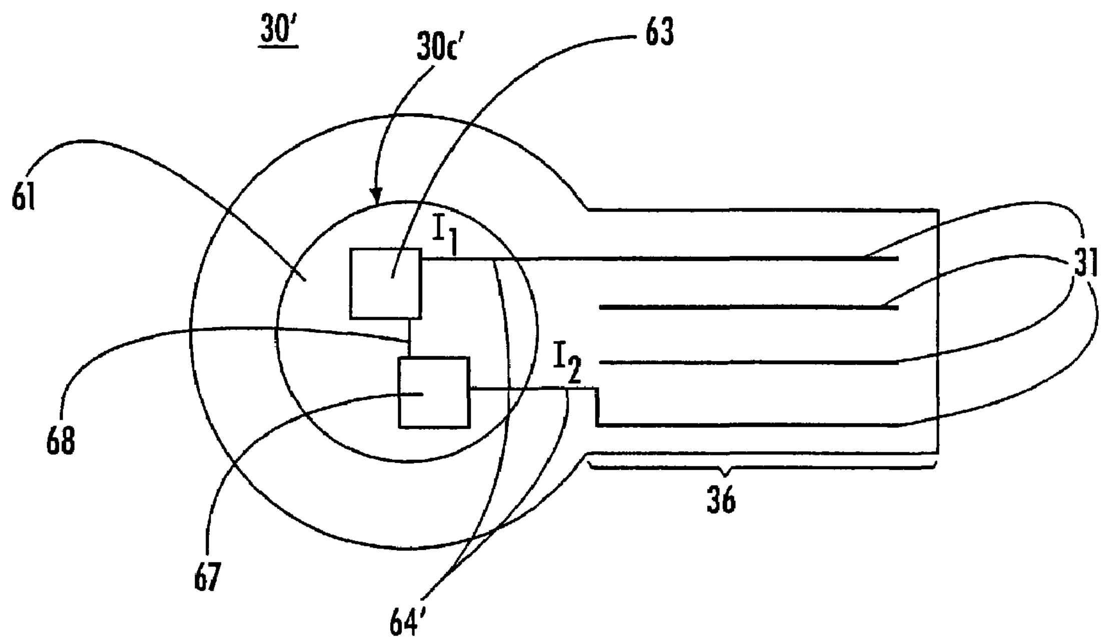
FIG. 9B is a schematic of further embodiments of a sensor patch with a circuit thereon according to embodiments of the present invention.

FIG. 9B is a top view of further embodiments of a sensor patch 30' that includes a tab portion 36 that is adapted to be received by a reader, for example, reader 75" illustrated in FIG. 7. As shown, the circuit 30*c*' includes a circuit layer 61 that includes at least one electrical contact 31 shown as a plurality of substantially parallel leads. During data readings/acquisitions, the sensor patch 30' is inserted into the reader port 32 of the reader 75" (FIG. 7) and the at least one electrical contact 31 is configured to provide the electrical connections between the operating circuitry on the circuit layer 61 and the external reader 75". The electrical contact(s) 31 may be covered with a protective upper layer 62 (FIG. 8A). If covered by an upper layer 62 that is a protective coating or other non-conductive insulator material, the clinician may need to form an opening into the coating or upper layer over the electrical contact(s) 31 so these contact(s) 31 may make electrical contact with the reader via sensor port 32 (FIG. 7).

FIG. 9B further illustrates the circuit layer 61 that includes the radiation sensitive operative sensor patch circuitry 30*c*'. The sensor patch circuitry 30*c*' includes a radiation sensitive device 63 that exhibits a detectable operational change when exposed to radiation and may include a memory device 67. In certain embodiments, the radiation sensitive device 63 is a miniaturized semiconductor component such as a MOSFET. Suitable MOSFETs include RADFETs available from NMRC of Cork, Ireland. In certain embodiments, the MOSFET may be sized and configured to be about 1-2 mm in width and length. The circuitry 30*c*' also includes at least one conductive lead or trace 64' extending from the radiation sensitive device 63 and/or the memory device 67 to the at least one electrical contact(s) 31. The traces or leads 64' may be formed, placed, or deposited onto the substrate layer 60 in any suitable manner including, but not limited to, applying conductive ink or paint or metal spray deposition on the surface thereof in a suitable metallic pattern, or using wires. As desired, an upper layer 62 such as described above (such as epoxy) may be formed over the circuit layer 61 (or even the entire sensor patch). Each sensor patch 30 may be from about 0.25 to about 1.5 inches long and wide and have a thin thickness of from about 1 to about 5 mm or less.

Figure 9C:
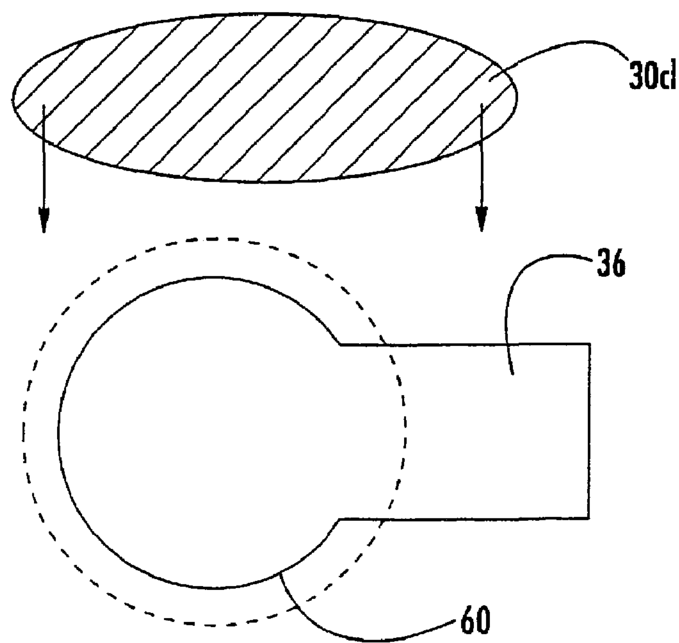
FIG. 9C is a schematic of further embodiments of a sensor patch with a circuit thereon according to embodiments of the present invention.
Figure 9D:
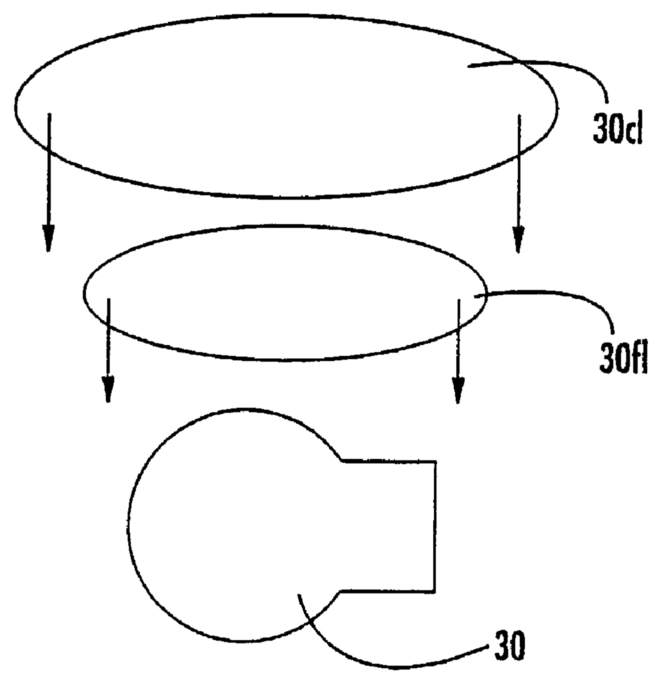
FIG. 9D is a schematic of further embodiments of a sensor patch according to embodiments of the present invention.
Figure 9E:
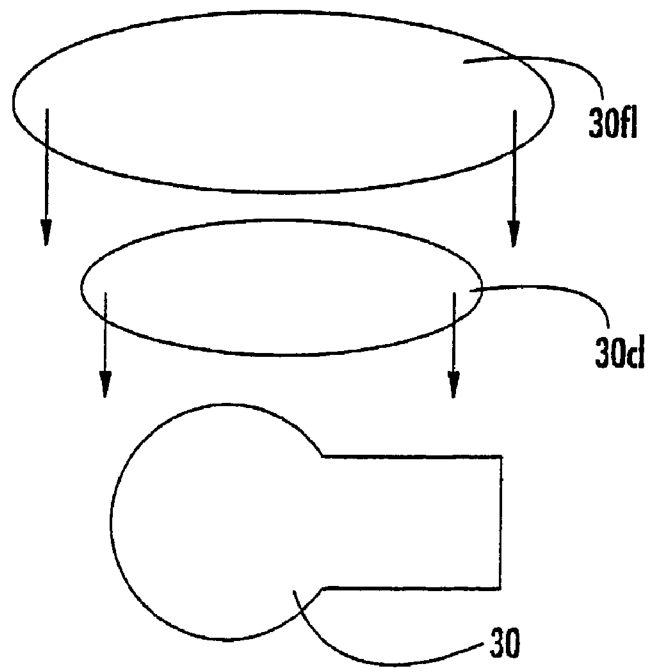
FIG. 9E is a schematic of further embodiments of a sensor patch according to embodiments of the present invention.

As discussed above with respect to FIG. 8A, the underside or bottom of the sensor patch 30*b* may include a releasable adhesive 30*a* so as to be able to attach to the skin of the patient. The adhesive 30*a* can be a medical grade releasable adhesive to allow the sensor patch 30 to be secured to the skin during the treatment session and then easily removed without harming the skin. The adhesive 30*a* can be applied to portions, or all, of the bottom surface of the substrate layer 60. Referring now to FIG. 9C, in certain embodiments, the underside of the sensor patch 30*b* may be free of the adhesive. As illustrated, an adhesive coverlay 30*cl* may be placed over the entire body of the sensor patch 30 to secure the sensor patch 30 to the patient. As further illustrated, the adhesive coverlay 30*cl* may be sized to extend beyond the outer perimeter of the sensor substrate 60 and leave the tab portion 36 of the sensor 30' exposed. The adhesive provided on the underside of the coverlay 30*cl* may be provided on a portion of the coverlay 30*cl*, for example, the portion of the coverlay 30*cl* contacting the patient's skin outside the perimeter of the sensor substrate 60, or on the entire underside of the coverlay 30*cl*.

Figure 10A:
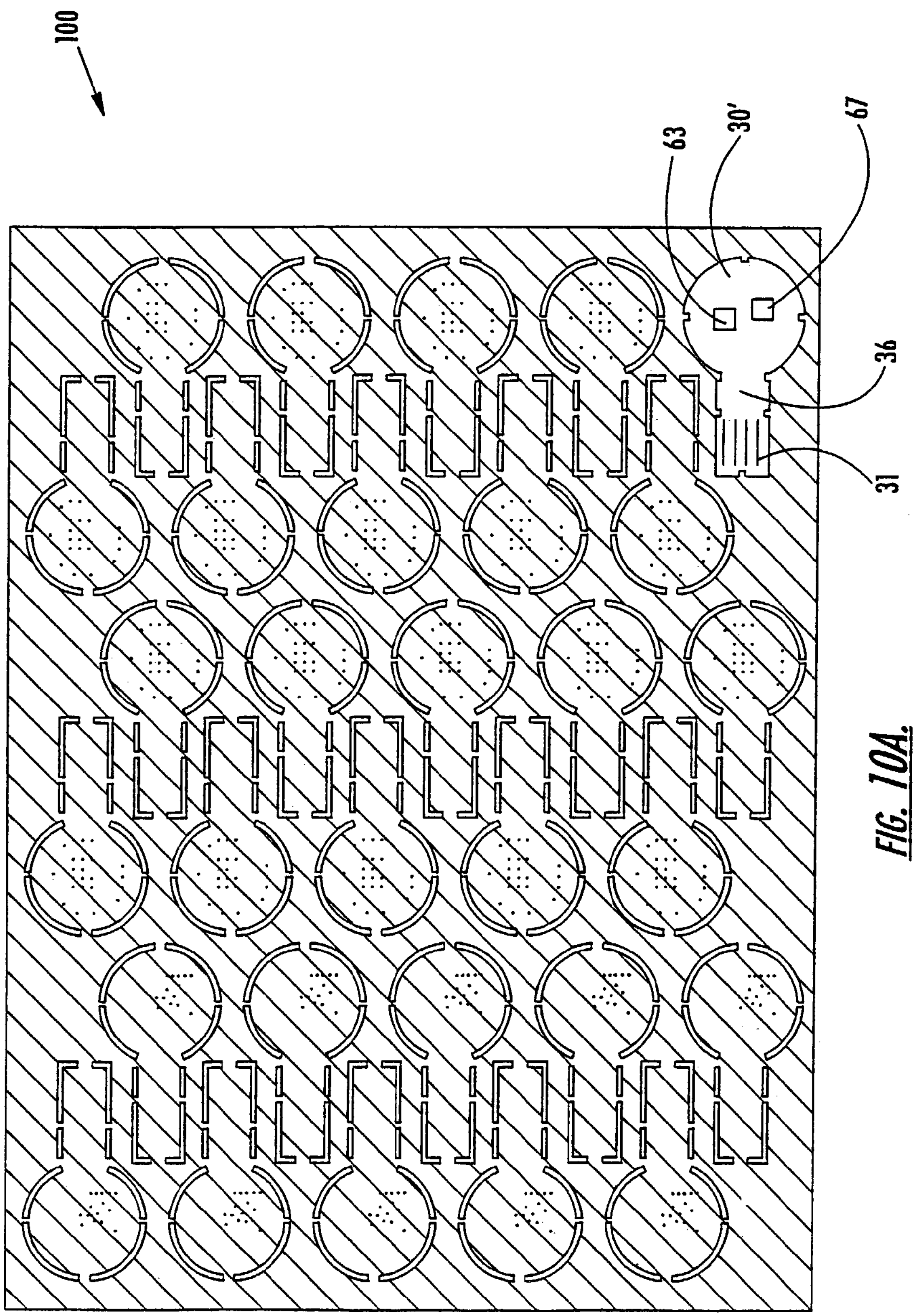
FIG. 10A is a schematic illustration of a sheet of sensors according to embodiments of the present invention.
Figure 10B:
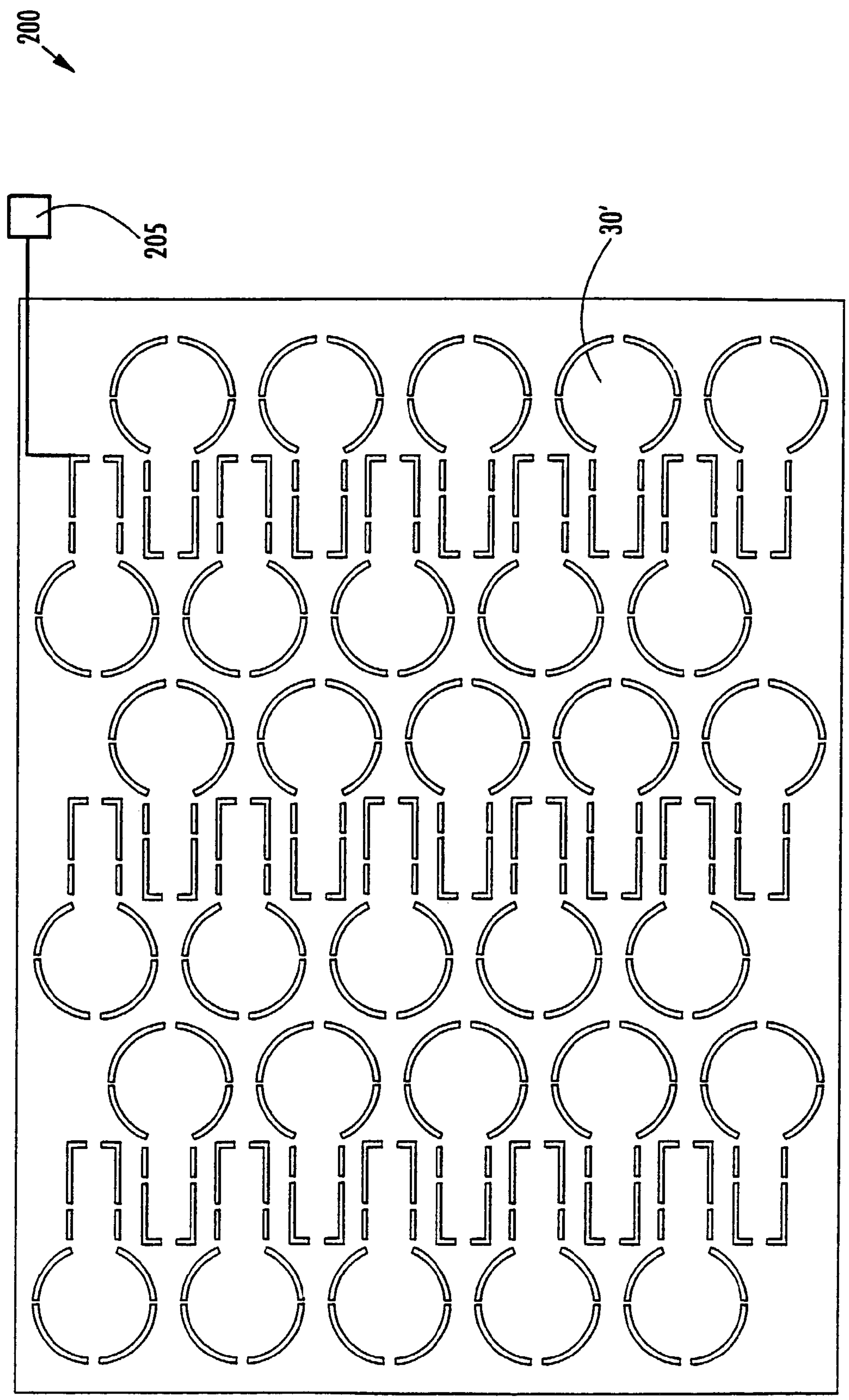
FIG. 10B is yet another schematic illustration of a sheet of sensors according to embodiments of the present invention.

Sensor patches 30 according to embodiments of the present invention may be provided individually or in sheets containing multiple sensor patches 30. In particular, the sensor patches 30 may be fabricated in high-density sheets. As used herein, "high density" refers to multiple sensor patches provided on a unitary sheet. High density is intended to encompass very large sheets containing, for example, hundreds or thousands of sensors, as well as, for example, 3×3 regions of these very large sheets typically including 6 or more sensors per region. Providing the sensor patches 30 including memory devices 67, for example EEPROMs, on high density sheets 200 as illustrated in FIGS. 10A and 10B provide the capability of calibrating and/or pre-dosing the entire sheet of sensor patches 30 at one time. As shown in FIG. 10A, the sheets 200 may include perforations for subsequent separation of the individual sensor patches 30 from the high density sheet 200. In certain embodiments, the sheet of sensor patches 200 may include from about 30 to about 100 sensor patches 30 per sheet. In other embodiments, multiple patches 30 may be provided per square inch of the high density sheet 200 and/or multiple patches 30, typically at least 6 patches, may be provided in a 3 by 3 inch region of the high density sheet.

Figure 10C:
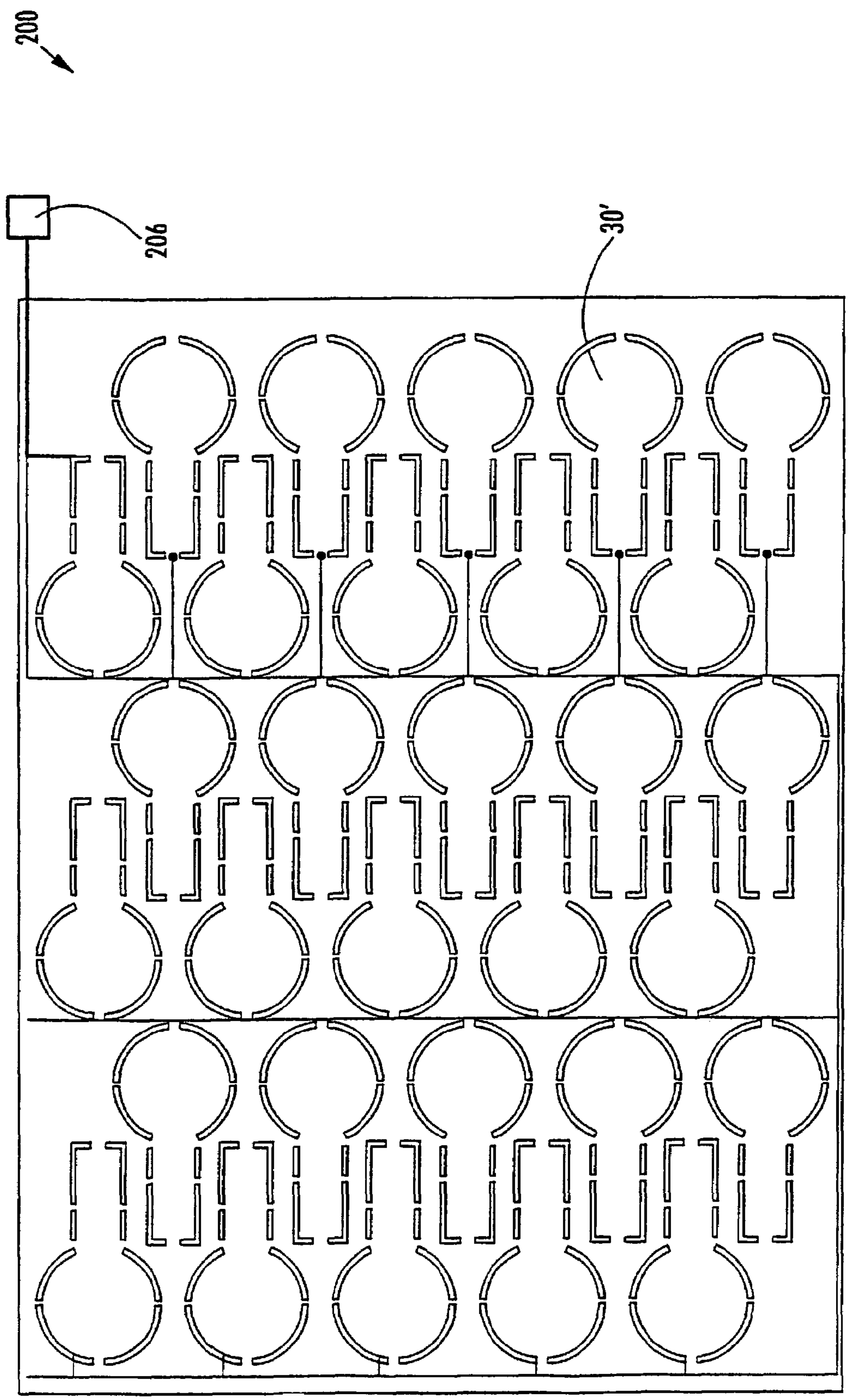
FIG. 10C is a further schematic illustration of a sheet of sensors according to embodiments of the present invention.

The sensor patches 30 may be calibrated at the factory or OEM. Each of the sensor patches 30 or the entire sheet 200 of sensor patches 30 may be calibrated by providing a wire(s) 205 illustrated in FIG. 10B that electrically couples each of the sensor patches 30 on the sheet 200. For ease of reference, only a single electrical line to one sensor is shown on FIG. 10B. The calibration data may be provided to the sensor patches 30 through the wire(s) 205 and may be stored in the memory storage device 67 of the sensor patch 30. The ability to calibrate a plurality of sensor patches 30 simultaneously may provide more precision in the dosimetry process and, therefore, possibly more reliable results. It will be understood that the sensor patches 30 may each have a dedicated wire or the sheet can have a calibration line all connected to a common lead 206 as shown in FIG. 10C that may be used to calibrate and/or pre-dose the sensor patches 30 individually.

As discussed above, the sensor patches 30 may be pre-dosed, i.e. dosed prior to placement on the patient. Dosing a sensor patch may include, for example, setting the amount of radiation to be delivered to a patient and the particular region (s) on the patient to which the radiation should be delivered. This process is typically performed by a physicist and can be very time consuming. The possibility of accurately pre-dosing a sensor patch 30 may significantly reduce the need for a physicist to be involved in the dosimetry confirmation process. In other words, using reliable dose patches can reduce the time a physicist expends to confirm the treatment beam and path dose.

It will be understood that sensor patches 30 adapted to be received by a reader 75 are not limited to the configuration illustrated in the figures provided herein. These figures are provided for exemplary purposes only and are not meant to limit the present invention. For example, the sensor patch 30' of FIG. 9B can be configured with a geometry that allows it (entirely or partially) to be received by a reader 75". The insertable geometry may take the form of an elongated tab, one end of the tab containing the radiation sensitive circuitry as well as the memory and the other end of the tab containing the electrical contacts for insertion into the reader device (not shown).

Figure 11:
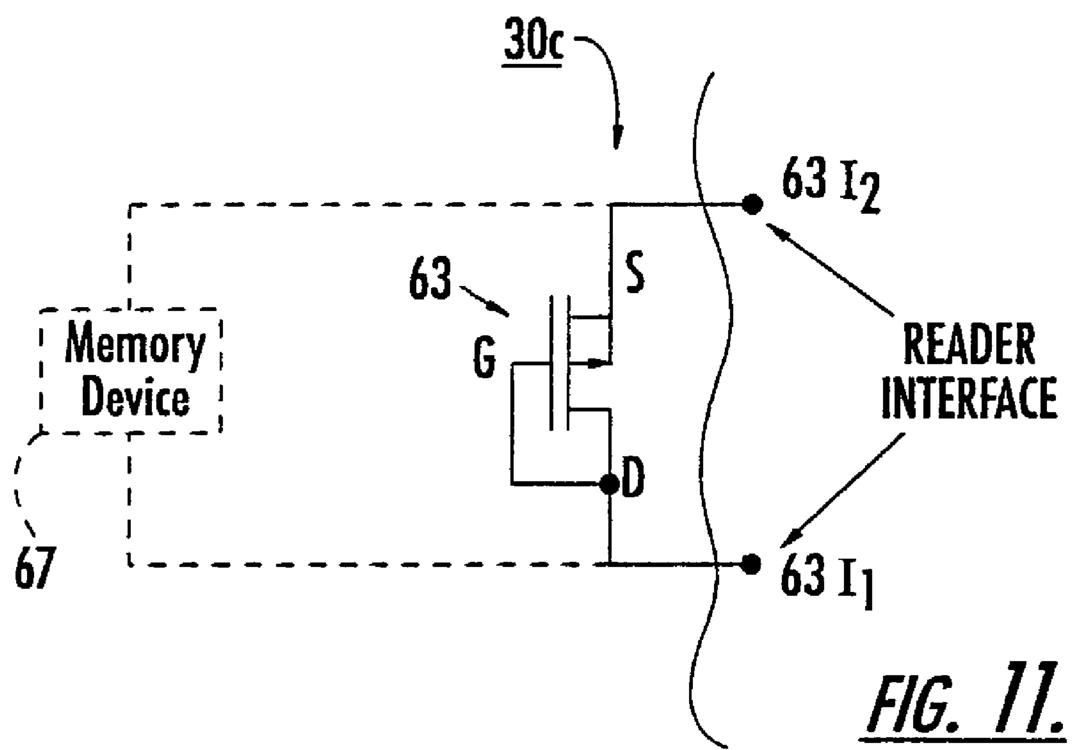
FIG. 11 is a schematic of a circuit diagram of a MOSFET sensor with a reader interface and an optional memory according to embodiments of the present invention.
Figure 12A:
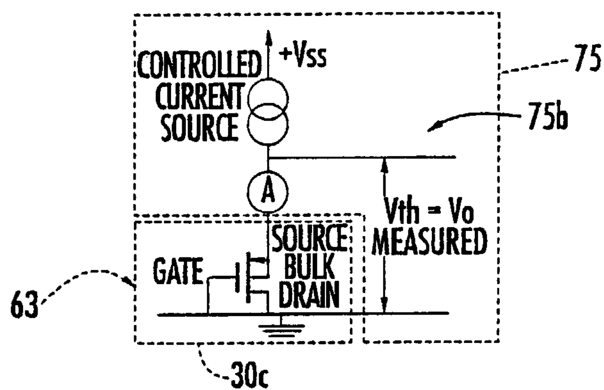
FIG. 12A is a schematic of a threshold voltage reader circuit according to embodiments of the present invention.

As shown in FIG. 11, in certain embodiments, the radiation sensitive device 63 is a RADFET. The RADFET can be biased with a gate/drain short so that it acts as a two-terminal device. FIG. 11 illustrates a portion of the circuit 30*c* with a RADFET 63 and two associated reader 75 interface or contact points 63$I_1$, 63$I_2$. FIG. 12A illustrates a reader 75 (upper broken line box) and the circuit 30*c* (lower broken line box) with the RADFET 63 configured with a gate to drain short. As shown, the reader 75 can include a RADFET bias circuit 75*b* that includes a controlled current source to allow a voltage reading to be obtained corresponding to the threshold voltage of the RADFET.

Figure 12B:
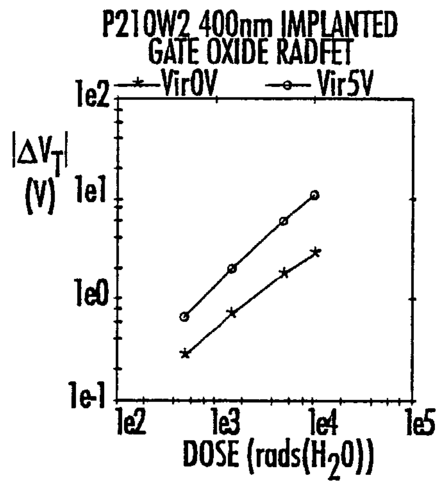
FIG. 12B is a graph of the change in the threshold voltage value versus radiation dose according to embodiments of the present invention.

As shown by the graph in FIG. 12B, changes in surface state charge density induced by ionizing radiation causes a shift in threshold voltage in the RADFET. FIG. 12B illustrates a radiation response of a standard P210W2 400 nm implanted gate oxide RADFET with lines for 0V (the-0-marked line) and 5V (the line with the -*-markings) irradiation bias responses. To obtain the amount of threshold voltage ("Vth") shift, the Vth value (zero dose) can be subtracted from the post-irradiation value and the calibration curve used to determine radiation dose. The calibration curve can be preloaded into the controller of the reader or a computer to provide the dose data. In certain embodiments, when obtaining the readings, the clinician may wear grounding straps to reduce static sensitivity of the circuitry. In certain embodiments, such as where contact points are exposed, ESD protection may be integrated into the sensor patch 30 itself.

As shown in FIG. 12A, the Vth change can be measured by determining the change in applied gate voltage necessary to induce a set current flow. As noted above, the RADFET characterization data can be obtained prior to exposure to radiation (zero dose). Thus, the starting threshold voltage of the sensor patch 30 will be known from a priori information (or can be obtained by the clinician prior to placing on the patient or after on the patient but before radiation exposure) and can be placed in the reader 75 or computer associated or in communication therewith.

Figure 13:
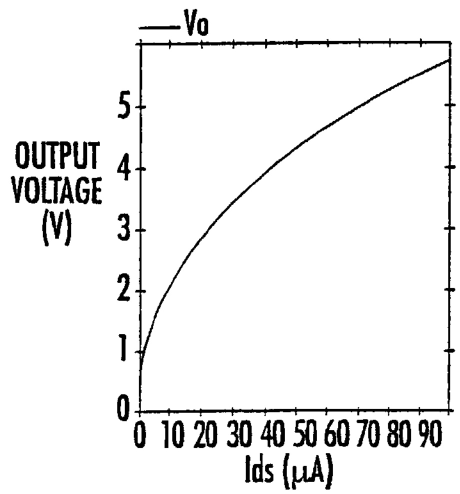
FIG. 13 is a graph of the threshold voltage dependence on Ids using the voltage ($V_0$) of the reader illustrated in FIG. 12A.

FIG. 13 illustrates the threshold voltage relationship between output voltage (voltage) and current Ids (the electrical current, drain-to source, in microamps) as measured using the output voltage of the reader circuit shown in FIG. 12A. In operation, the reader circuit is configured to contact the sensor to provide a constant current source to the circuit so as to be able measure Vth at a substantially constant or fixed bias condition.

Figures 14A, 14B:
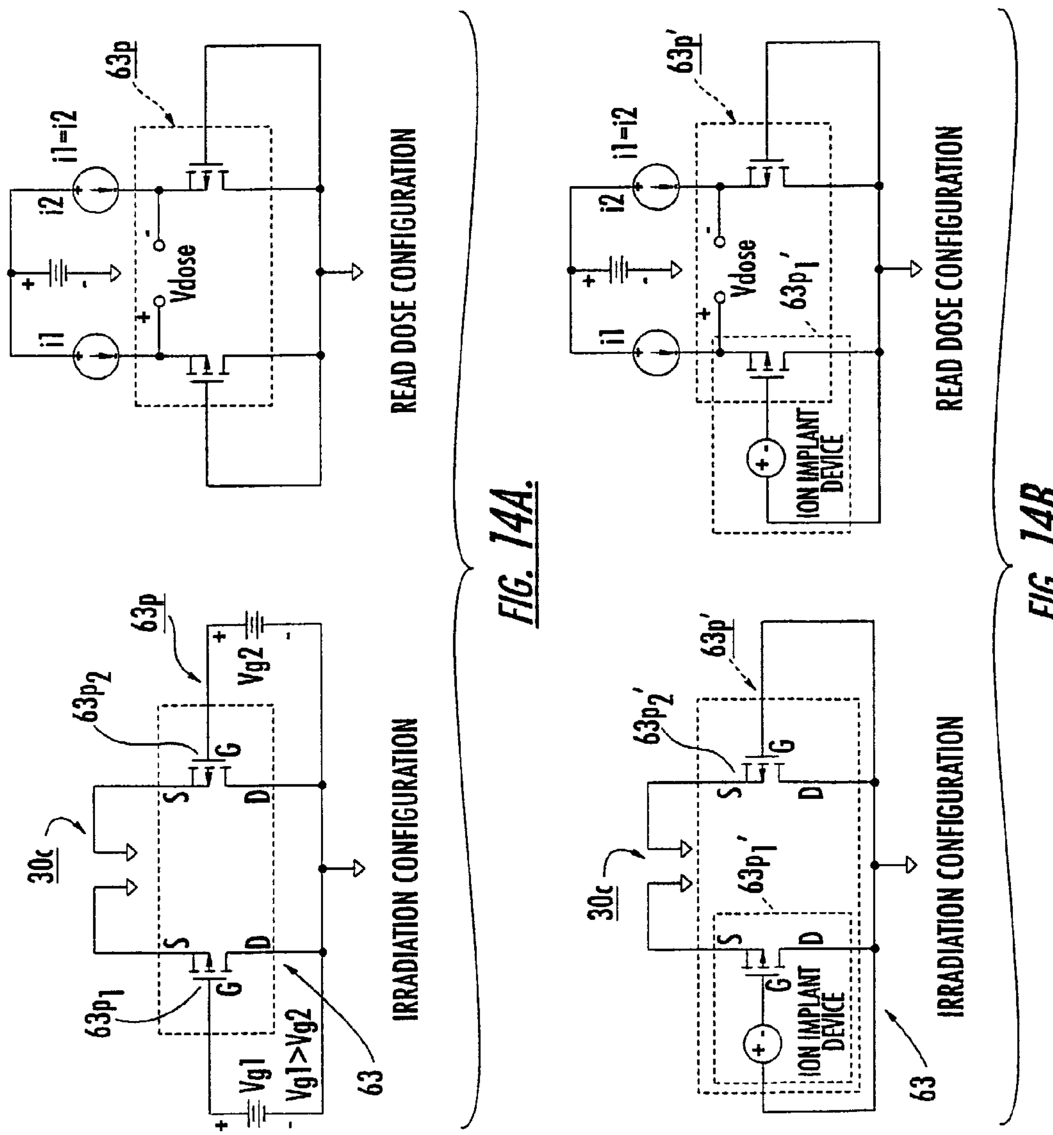
FIG. 14A is a schematic of a circuit diagram with a MOSFET pair, the left side of the figure corresponding to an irradiation operative configuration and the right side of the figure corresponding to a read dose operative configuration, according to embodiments of the present invention.
FIG. 14B is a schematic of a circuit diagram with a MOSFET pair, the left side of the figure corresponding to an irradiation operative configuration and the right side of the figure corresponding to a read dose operative configuration, according to other embodiments of the present invention.

FIGS. 14A and 14B illustrate alternate embodiments of MOSFET based circuits 30*c*. Each circuit 30*c* employs a RADFET pair 63*p* (FIG. 14A), 63*p'* (FIG. 14B) as the radiation sensitive device 63. The configuration on the left of each of these figures illustrates the irradiation configuration and the configuration on the right illustrates the read dose configuration. In the embodiment shown in FIG. 14A, the RADFET pair 63*p* are differentially biased during irradiation to create different voltage offsets. Each of the RADFETs in the pair 63$p_1$, 63$p_2$ can be differentially biased during radiation to generate different voltage offsets when exposed to radiation. Using a pair of RADFETS can reduce the influence of temperature in the detected voltage shift value. In particular embodiments, the RADFET pair can be matched (such as taken from the same part of the substrate during fabrication) to reduce drift effects (Vth drift). In certain embodiments, the voltage reading can be obtained with a zero bias state, and/or without requiring wires during radiation, and/or without requiring a floating gate structure.

In the embodiment shown in FIG. 14B, one of the RADFETs 63$p_1'$ in the pair 63*p* is selectively implanted with dopant ions to shift the threshold voltage (Vth) of that RADFET with respect to the other RADFET 63$p_2'$. The ion implantation can be carried out in various manners as known to those of skill in the art, such as by masking one of the FETs with photoresist to inhibit ions from entering into the gate region. As is well known, using the proper implant species and/or dopant material can increase the FET sensitivity to radiation effects. In certain embodiments of the present invention, a MOSFET (RADFET) pair is used to effectively provide "differential biasing" without the need to apply an external voltage and without the need for a floating gate structure. That is, the MOSFETs can be configured to be individually unbiased and readings of the two MOSFETs (one at a different threshold voltage value) generates the differential biasing. In particular embodiments, this radiation sensitive MOSFET pair configuration that does not require floating gate structures and/or external voltage can be used in implantable as well as skin mounted sensors, such as in implantable sensors used as described in U.S. Pat. No. 6,402,689 to Scarantino et al.

Figure 15C:
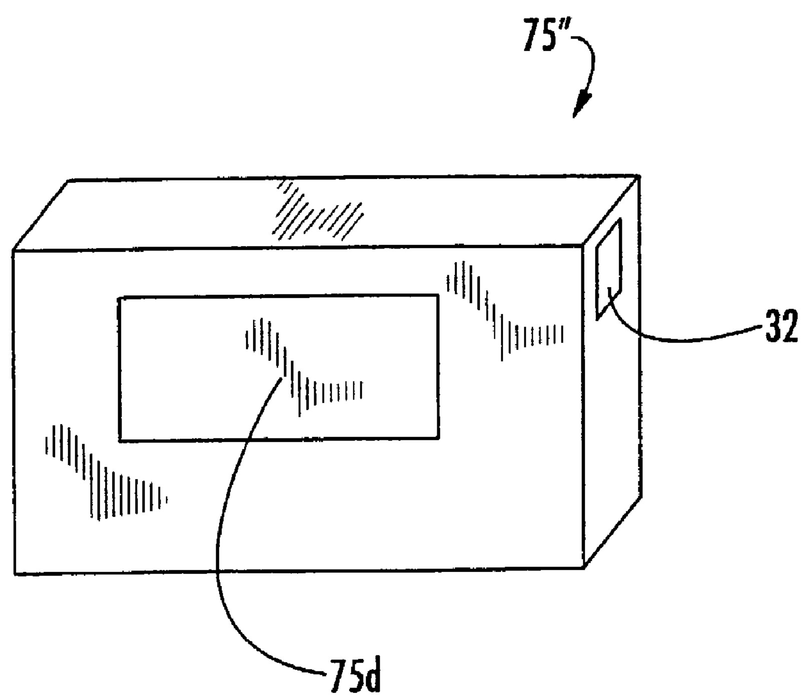
FIG. 15C is a block diagram illustrating a reader device according to further embodiments of the present invention.

FIG. 15A illustrates embodiments of a radiation dose evaluation system 15 according to embodiments of the present invention. As shown, the system 15 includes a reader 75 and a set of radiation sensor patches 130'. The reader 75 may include, for example, the reader 75' of FIG. 15B or the reader 75" of FIG. 15C. The sensor patches 30 can be arranged as a strip of patches 30 held in a single-patient sized package 130*p*. As before, the package 130*p* may also include bar coded radiation calibration characterizing data labels 132 for the sensor patches 30 and/or a memory 167 in each or selected memory patches 30. The reader 75' as shown in FIG. 15B can include the probe 75*p*, an optical wand 75*w* and a display screen 75*d*. The reader 75" as shown in FIG. 15C can include a sensor port 32 and a display screen 75*d*. The reader 75 can also include a RADFET bias circuit 75*b*. In certain embodiments, the reader 75 is a portable flat pocket or palm size reader that a clinician can carry relatively non-obtrusively in his/her pocket or a similar sized casing.

As shown by the dotted line boxes in FIG. 15A, the reader 75 may hold a power source 78 and plurality of operational software modules including: an optical bar code reader module 76, a zero-dose threshold voltage data module 77, a radiation dose conversion module (based on a predetermined voltage threshold to radiation dose response curve) 79, and a threshold voltage post radiation data module 80.

In operation, the reader 75 can be configured to supply a bias current to the RADFET by attaching to the sensor patch 30 and electrically contacting the conductive probe region 30*p* or the electrical contacts 31. The reader 75 can measure the voltage shift response of the RADFET on the sensor patch 30 and calculate radiation dose based on the shift and the dose conversion algorithm. The reader 75 can display the results to the clinician (such as on an integrated LCD screen 75*d* incorporated into the body of the reader) and may be configured to download or upload the data to another device (such as a computer or computer network) for electronic record generation or storage.

The dose amount can be calculated for each sensor patch 30 used. In particular embodiments, the system can be configured to generate an average or weighted average of the dose amount determined over a plurality of the patches. In certain embodiments, where there is a large variation in values (or if it departs from a statistical norm or predicted value) the system can be configured to discard that sensor value or to alert the clinician of potential data corruption. Of course, much smaller values are predicted in sensitive areas away from the targeted zone and the system can be configured to evaluate whether the sensor is in a primary location or in a secondary zone as regards the radiation path.

It is noted that features described with respect to one embodiment of the sensor, reader and/or system may be incorporated into other embodiments and the description and illustrations of such features are not be construed as limited to the particular embodiment for which it was described.

As will be appreciated by one of skill in the art, the present invention may be embodied as a method, data or signal processing system, or computer program product. Accordingly, the present invention may take the form of an entirely hardware embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as LABVIEW, Java®, Smalltalk, Python, or C++. However, the computer program code for carrying out operations of the present invention may also be written in conventional procedural programming languages, such as the "C" programming language or even assembly language. The program code may execute entirely on the user's computer, partly on the user's computer, as a standalone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Figure 16:
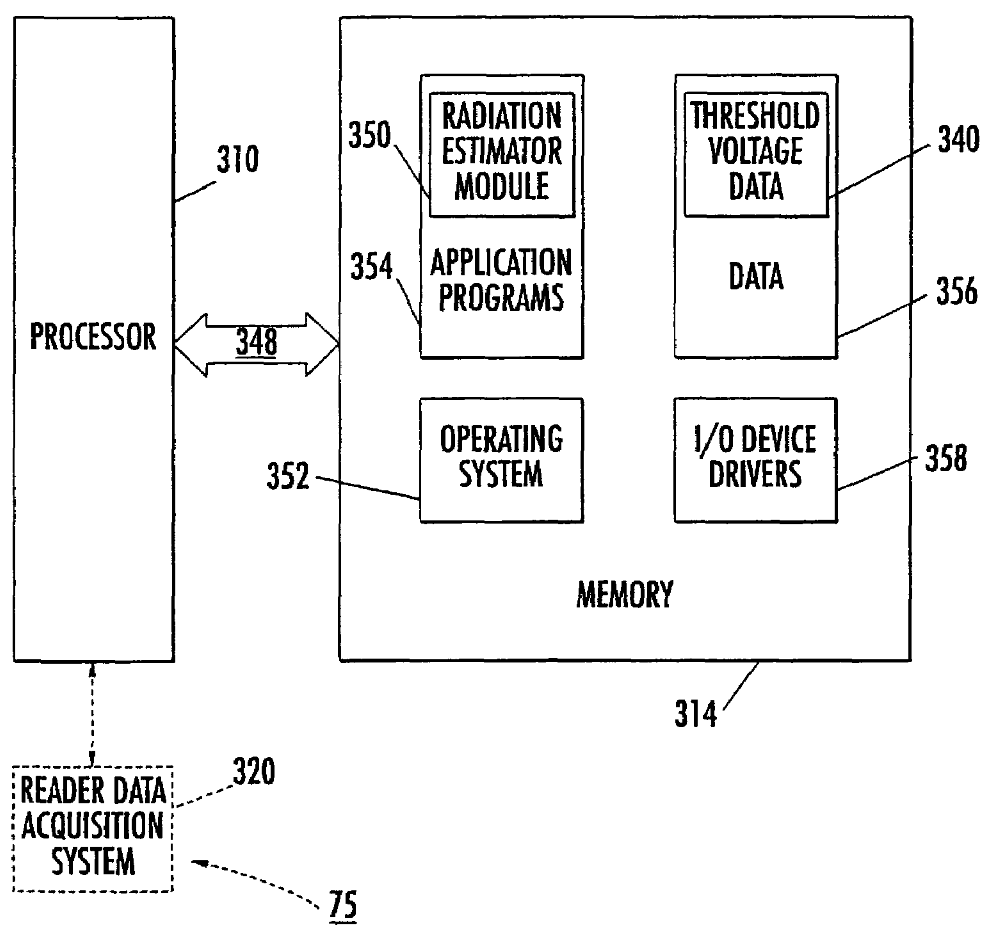
FIG. 16 is a block diagram of a computer program having a radiation estimation module according to embodiments of the present invention.

FIG. 16 is a block diagram of exemplary embodiments of data processing systems that illustrate systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system. The memory 314 can include, but is not limited to, the following types of devices: cache, ROM, PROM, EPROM, EEPROM, flash memory, SRAM, and DRAM.

As shown in FIG. 16, the memory 314 may include several categories of software and data used in the data processing system 305: the operating system 352; the application programs 354; the input/output (I/O) device drivers 358; a radiation estimator module 350; and the data 356. The data 356 may include threshold voltage data 340 (zero dose and post irradiation dose levels) which may be obtained from a reader data acquisition system 320. As will be appreciated by those of skill in the art, the operating system 352 may be any operating system suitable for use with a data processing system, such as OS/2, AIX, OS/390 or System390 from International Business Machines Corporation, Armonk, N.Y., Windows CE, Windows NT, Windows95, Windows98, Windows2000 or Windows XP from Microsoft Corporation, Redmond, Wash., Unix or Linux or FreeBSD, Palm OS from Palm, Inc., Mac OS from Apple Computer, or proprietary operating systems. The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and preferably include at least one application that supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the radiation estimator module 350 being an application program in FIG. 16, as will be appreciated by those of skill in the art, other configurations may also be utilized while still benefiting from the teachings of the present invention.

For example, the radiation estimation module 350 may also be incorporated into the operating system 352, the I/O device drivers 358 or other such logical division of the data processing system. Thus, the present invention should not be construed as limited to the configuration of FIG. 16, which is intended to encompass any configuration capable of carrying out the operations described herein.

In certain embodiments, the radiation estimation module 350 includes computer program code for estimating radiation dose based on the measured threshold voltage shift. The I/O data port can be used to transfer information between the data processing system and the reader data acquisition system 320 or another computer system or a network (e.g., the Internet) or to other devices controlled by the processor. These components may be conventional components such as those used in many conventional data processing systems that may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configurations illustrated in the figures but is intended to encompass any configuration capable of carrying out the operations described herein.

The flowcharts and block diagrams of certain of the figures herein illustrate the architecture, functionality, and operation of possible implementations of probe cell estimation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 17:
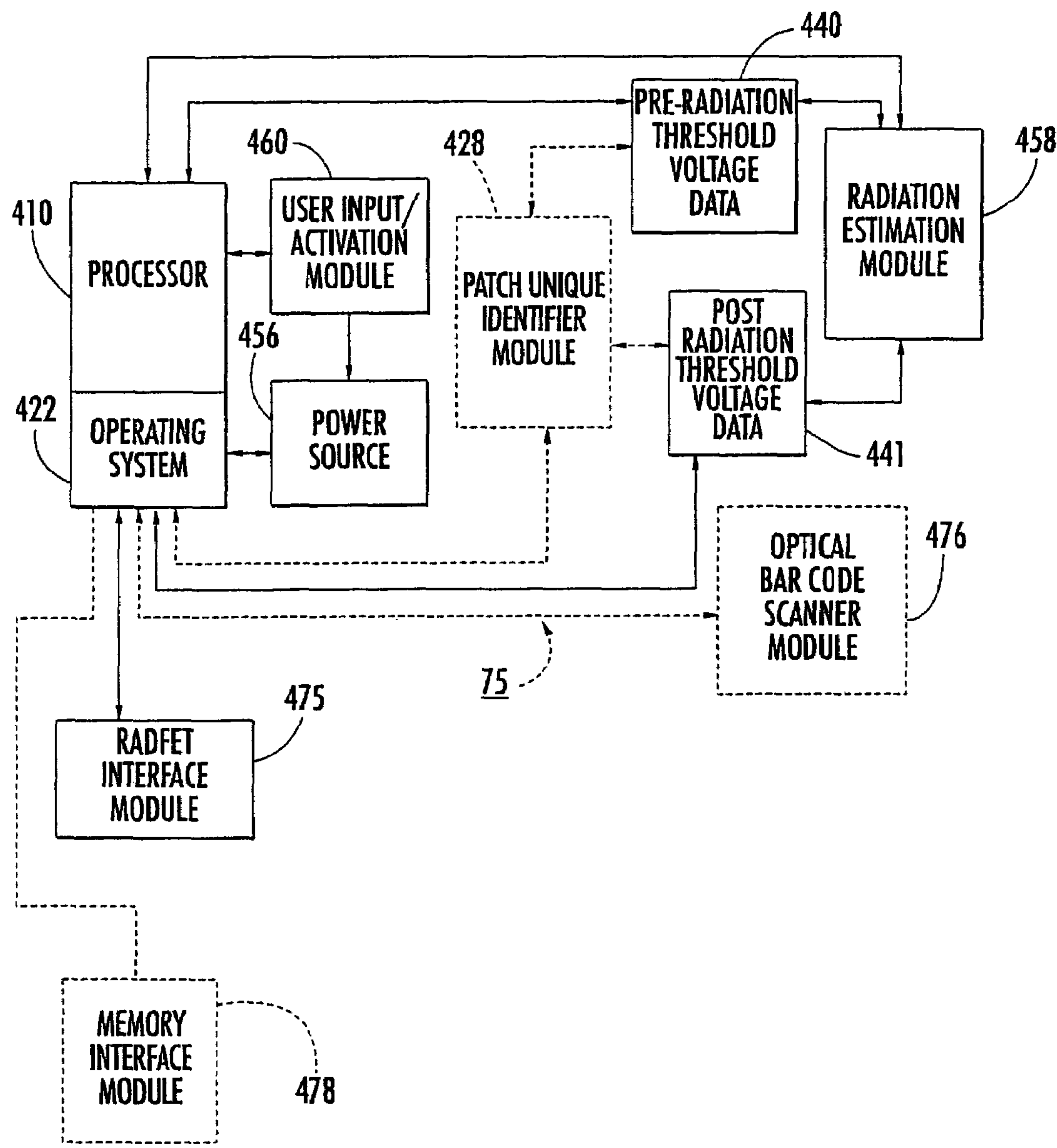
FIG. 17 is a block diagram of a point-contact reader data acquisition system according to embodiments of the present invention.

FIG. 17 is a block diagram illustration of one embodiment of a reader 75 according to the present invention. As shown, the reader 75 includes an operating system 422, a processor 410, a power source 456, and a user activation/input module 460. The reader 75 can also include a RADFET interface module 475 and a sensor patch memory interface module 478. In certain embodiments, the sensor patch 30 may be configured to communicate wirelessly with the reader 75. In these embodiments, the interface module 475 may be configured to receive wireless signals from the sensor patch 30. The reader 75 may optionally include a sensor patch identifier module 428 to track which sensor patch 30 has a particular radiation dose result. The identifier module 428 may allow the user to input via an input keypad associated with the reader, an alphanumeric identifier (F1, B1, etc.) for a particular sensor patch prior to obtaining the reading, or a bar code identifier or other automated identifier means can be used (such as scanning a bar code label on the sensor and the like).

The reader 75 also includes pre-radiation (zero dose) threshold voltage data 440, post radiation threshold voltage data 441, and a radiation estimation module 458. The radiation estimation module 458 may also be configured to extrapolate to arrive at the radiation dose delivered to the tumor site. As shown, the reader 75 may also include an optical bar code scanner module 476 to allow the reader to input the characterizing zero dose threshold voltage values by optically reading same. Similarly, calibration data can be entered via the bar the bar code scanner 476 or memory 67 from the patches 30. Alternatively, the clinician can enter the desired data in situ as desired.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for monitoring radiation doses administered to patients undergoing radiation treatments, comprising the steps of:

releasably securing at least one single-use dosimeter sensor patch comprising an electronic memory held thereon, the patch secured to be in intimate contact with the skin of the patient such that during operation, the patch is self-contained and devoid of wires extending therefrom;

administering radiation to the patient in a first treatment session after the securing step;

contacting the self-contained sensor patch with a dose-reader device after the administering step to obtain data associated with a change in an operational parameter in the dosimeter sensor patch and to obtain data from the electronic memory; and determining the radiation dose received by the patient during the administering step based on the change in the operational parameter.

2. A method according to claim 1, wherein an underside of the patch comprises an adhesive, and wherein the releasably securing step is carried out by pressing the patch onto the skin so that it adheres thereto.

3. A method according to claim 1, wherein the releasably securing step is carried Out using an adhesive coverlay disposed over the sensor patch such that at least a portion of the adhesive coverlay contacts the skin and adheres the sensor patch thereto.

4. A method according to claim 1, further comprising at least one of calibrating and/or pre-dosing the at least one single-use dosimeter sensor patch before releasably securing the sensor patch onto the skin of the patient.

5. A method according to claim 4, wherein the calibrating step and/or pre-dosing step further comprises calibrating and/or pre-dosing a plurality of sensor patches simultaneously, wherein the plurality of sensor patches are disposed on a unitary sheet of sensor patches that are electrically coupled.

6. A method according to claim 1, further comprising storing the patient's determined radiation-dose data in the memory of the sensor patch.

7. A method according to claim 6, further comprising downloading the stored data to a remote computer and/or reader.

8. A method according to claim 1, further comprising sterilizing the single-use dosimeter sensor patch and applying an adhesive to a selected primary surface.

9. A method according to claim 8, further comprising packaging the single-use dosimeter patch in a sterile package suitable for human medical use.

10. A method according to claim 1, wherein the at least one single-use dosimeter patch is a plurality of low-profile discrete flexible single use patches, and wherein the step of releasably securing comprises positioning each patch in a different location about the targeted radiation zone on the patient.

11. A method according to claim 10, further comprising positioning at least one of the patches proximate to a region where radiation is not desired or in radiation sensitive region to detect whether radiation is received in the regions.

12. A method according to claim 10, further comprising:

positioning a second plurality of self-contained dosimeter sensor patches different from the first dosimeter patches to be in intimate contact with the skin of the patient during a second treatment session, the patches of the second plurality of patches comprising an electronic memory held thereon;

administering a second radiation therapy to the patient at a second treatment session;

contacting each of the second plurality of sensor patches with a dose-reader device after the administering step to obtain data associated with a change in an operational parameter in each respective dosimeter sensor patch and to obtain data from the electronic memory thereof; and determining the radiation dose received by the patient during the administering step based on the change in the operational parameter of the dosimeter sensor patches.

13. A method according to claim 12, further comprising:

disposing of the first plurality of dosimeter sensor patches after the first treatment session; and disposing of the second plurality of dosimeter patches after the second treatment session.

14. A method according to claim 12, further comprising:

storing the determined radiation dose of the first plurality of dosimeter sensor patches in the electronic memory of the respective patches after the first treatment session to form a patient record of radiation dose; and storing the determined radiation dose of the second plurality of dosimeter patches in the electronic memory of the respective patches after the second treatment session to form a patient record of radiation dose.

15. A method according to claim 12, wherein the patches are placed in substantially the same locations for the first and second treatments.

16. A method according to claim 10, wherein the determining step includes serially individually physically contacting the sensor patches with the dose-reader device to determine the radiation dose amount for each of the sensor patches.

17. A method according to claim 16, further comprising:

positioning a second plurality of self-contained dosimeter sensor patches onto the patient during a second treatment session subsequent to the first treatment session, the patches having an associated electronic memory thereon;

administering a second radiation therapy to the patient at a second treatment session; and electronically considering whether there is a different determined value at one or more patch locations between the first and second treatments to identify whether the radiation is properly focused.

18. A method according to claim 10, wherein the patient undergoing treatment has a targeted tumor treatment site, wherein the dosimeter patches are disposed about the tumor site on the front and back of the body, and wherein the dose amount delivered to the tumor site is estimated based on the determined values.

19. A method according to claim 10, further comprising electronically mapping a dose gradient by correlating the determined radiation dose values at each sensor patch to the anatomical location on the subject of each patch.

20. A method according to claim 10, wherein the determining step is carried out to calculate an average or weighted average of the dose amount based on the doses associated with the plurality of patches.

21. A method according to claim 1, wherein contacting the sensor patch with a dose-reader device comprises positioning the sensor patch in a sensor port of the dose-reader device such that there is an electrical coupling between the sensor patch and the dose-reader device.

22. A method according to claim 21, wherein the sensor patch has been adapted to be inserted into the dose-reader device and wherein the dose-reader device has been adapted to receive the sensor patch.

23. A method according to claim 1, wherein contacting the sensor patch with a dose-reader device comprises positioning the dose-reader device such that an electrical coupling is established between the sensor patch and the dose-reader device, wherein the sensor patch includes at least one electrical sensor contact to facilitate the electrical coupling.

24. A method according to claim 1, wherein the dosimeter patch sensor comprises a MOSFET device with an associated threshold voltage which changes when exposed to radiation, and wherein the determining step further includes the step of analyzing the change in the threshold voltage.

25. A method according to claim 24, wherein the method further comprises the step of determining a pre-radiation threshold voltage value stored in the electronic memory of the patch prior to the administering radiation step.

26. A method according to claim 25, further comprising delivering a first set-up verification non-therapeutic radiation dose and obtaining a first radiation dose value for at least one sensor patch after the at least one sensor patch is secured to the patient to confirm that a plurality of beam set-up parameters are correct and/or suitable.

27. A method according to claim 26, wherein the plurality of set-up beam parameters comprise at least one of beam energy, field size, surface to surface distance, electrons and photons.

28. A method according to claim 24, wherein the determining step comprises automatically reducing the value of the post-radiation threshold voltage by the pre-radiation threshold voltage value and electronically comparing to a dose curve to determine the radiation dose.

29. A method according to claim 1, wherein the step of contacting is carried out to obtain measurement methodology from the electronic memory.

30. A method according to claim 1, wherein the at least one patch is a plurality of patches, the method further comprising discarding a sensor patch radiation value or alerting a clinician of potential data corruption if a large variation in dose amount is determined between patches.

31. A method for monitoring radiation doses administered to patients undergoing radiation treatments, comprising the steps of:

releasably securing at least one single-use dosimeter sensor patch onto the skin of the patient such that the patch is self-contained and devoid of wires extending therefrom;

providing an overlay material over the surface of the sensor patch to simulate a subsurface placement of the sensor patch corresponding to a desired distance beneath the skin of the patient;

administering radiation to the patient in a first treatment session;

contacting the sensor patch with a dose-reader device after the administering step to obtain data associated with a change in an operational parameter in the dosimeter sensor patch; and determining the radiation dose received by the patient during the administering step based on the change in the operational parameter

32. A method according to claim 31, wherein the overlay material is configured to be integrated with the sensor patch.

33. A method according to claim 31, wherein the overlay material comprises a resilient, flexible, skin-like material.

34. A method according to claim 31, wherein forming the overlay material comprises forming the overlay material having a thickness of from about 0.5 to about 3 cm.

35. A method according to claim 34, wherein forming the overlay material comprises forming the overlay material having a thickness of from about 1 to about 1.5 cm.

36. A system for monitoring radiation administered to a patient during a therapeutic treatment, the system comprises:

at least one single-use self-contained dosimeter patch, the patch comprising a body configured to be in intimate contact with skin of a patient, the patch holding a circuit with at least one MOSFET and an external reader contact region thereon, the at least one MOSFET having an associated threshold voltage that changes when exposed to radiation, the body comprising opposing upper and lower primary surfaces; and an external portable dose-reader being configured to make electrical contact with the patch by physically engaging with the contact region on the patch to obtain voltage threshold data corresponding to the dose amount of radiation exposure it is exposed to in use, wherein the patch has a perimeter that is devoid of outwardly extending loose lead wires.

37. A system according to claim 36, wherein the at least one patch comprises a tab portion that is configured to be inserted in the external portable dose reader and to make electrical contact therewith.

38. A system according to claim 37, wherein the external portable dose-reader comprises a sensor port, the senor port being configured to receive the tab portion of the patch and make electrical contact therewith to obtain the threshold voltage value associated with the patch.

39. A system according to claim 36, wherein the at least one dosimeter patch is a plurality of discrete sensor patches. each having a substantially conformable resilient body that adhesively attaches to the skin of the patient.

40. A system according to claim 36, wherein the at least one dosimeter patch is a plurality of discrete sensor patches having a substantially conformable resilient body, and wherein the patches are configured to be used concurrently at multiple different positions on the patient.

41. A system according to claim 40, wherein the reader is configured to electronically consider whether there is a different determined value at one or more patch locations to identify whether the radiation is properly focused.

42. A system according to claim 36, wherein the reader has a probe end portion that is configured to penetrate or pierce the body of the patch to make direct electrical contact with the circuit at the reader contact region.

43. A system according to claim 36, wherein the reader further comprises a display for outputting the calculated dose amount, and wherein the reader is configured to serially contact with each respective sensor patch to obtain the threshold voltage value associated therewith before and after use in active radiation therapy.

44. A system according to claim 36, wherein the reader comprises data transfer means to transmit the calculated dose amount to a local or remote controller for electronic storage into a patient's records.

45. A system according to claim 36, wherein the patch further comprises an electronic memory storage device that is electrically coupled to the at least one MOSFET, the memory storage device including patient information.

46. A system according to claim 45, wherein the memory storage device comprises an EEPROM.

47. A system according to claim 45, wherein the memory storage device comprises data corresponding to an electronic bias parameter for radiation quantification.

48. A system according to claim 45, wherein the at least one patch is at least one of pre-dosed and/or calibrated prior to placing the at least one patch on the patient and wherein the pre-dosing and/or calibration data is stored in the memory storage device of the patch.

49. A system according to claim 48, wherein a plurality of patches are provided on a unitary sheet, the sheet of patches being at least one of pre-dosed and/or calibrated simultaneously, and wherein the pre-dosing and/or calibration data is stored in the memory storage device of the respective patches.

50. A system according to claim 36, wherein the at least one patch is a plurality of patches, and wherein the dose reader is configured to determine a radiation value for each patch and a delivered dose for each treatment session, the patch being configured to measure between about 1.8-2 Gray per session.

51. A system according to claim 50, wherein the at least one patch is a plurality of patches, and wherein the dose reader is configured to evaluate the individual radiation dose amounts for each patch during each session to generate confirmation of delivered cumulative doses in the range of between 35-80 Gray.

52. A system according to claim 36, wherein the lower primary surface of the patch comprises a medical grade adhesive thereon.

53. A system according to claim 36, wherein the patch comprises a coverlay that includes a medical grade adhesive that is configured to overlie the circuit substrate and hold the sensor patch in position on the patient.

54. A system according to claim 36, wherein the at least one patch is a plurality of patches, and wherein the dose reader is configured to calculate an average or weighted average of the dose amount based on the doses associated with the plurality of patches.

55. A system according to claim 36, wherein the at least one patch is a plurality of patches sealed in at least one sterile package.

56. A system according to claim 36, wherein the at least one patch further comprises an electronic memory storage device configured to electronically store a patients radiation dose data to provide a patient radiation dose record.

57. A system according to claim 36, wherein the at least one patch further comprises an electronic memory storage device configured to electronically store calibration data and measurement methodology of a respective patch readable by the external reader.

58. A system according to claim 36, wherein the reader is configured to evaluate whether the sensor is in a targeted zone of a radiation path to determine if a radiation value departs from a predicted value or statistical norm.

59. A system for monitoring radiation administered to a patient during a therapeutic treatment, the system comprises:

at least one single-use dosimeter patch, the patch comprising a body holding a circuit with at least one MOSFET and an external reader contact region thereon, the at least one MOSFET having an associated threshold voltage that changes when exposed to radiation, the body comprising opposing upper and lower primary surfaces; and an external portable dose-reader being configured to make electrical contact with the patch by physically engaging with the contact region on the patch to obtain voltage threshold data corresponding to the dose amount of radiation exposure it is exposed to in use, wherein the patch has a perimeter that is devoid of outwardly extending loose lead wires, and wherein the at least one MOSFET includes a MOSFET pair, wherein the MOSFET pair are differentially biased during irradiation to create different voltage offsets.

60. A system for monitoring radiation administered to a patient during a therapeutic treatment, the system comprises:

at least one single-use dosimeter patch, the patch comprising a body holding a circuit with at least one MOSFET and an external reader contact region thereon, the at least one MOSFET having an associated threshold voltage that changes when exposed to radiation, the body comprising opposing upper and lower primary surfaces; and an external portable dose-reader being configured to make electrical contact with the patch by physically engaging with the contact region on the patch to obtain voltage threshold data corresponding to the dose amount of radiation exposure it is exposed to in use, wherein the patch has a perimeter that is devoid of outwardly extending loose lead wires, and wherein the at least one MOSFET includes a MOSFET pair, wherein one of the MOSFETs in the pair is selectively implanted with dopant ions to shift the threshold voltage with respect to the other MOSFET and/or to increase the radiation sensitivity of the implanted MOSFET relative to the other MOSFET.

61. A system for monitoring radiation administered to a patient during a therapeutic treatment, the system comprises:

at least one single-use dosimeter patch, the patch comprising a body holding a circuit with at least one MOSFET and an external reader contact region thereon, the at least one MOSFET having an associated threshold voltage that changes when exposed to radiation, the body comprising opposing upper and lower primary surfaces;

an overlay material over the surface of the at least one sensor patch to simulate a subsurface placement of the at least one sensor patch corresponding to a desired distance beneath the skin of the patient; and an external portable dose-reader being configured to make electrical contact with the patch by physically engaging with the contact region on the patch to obtain voltage threshold data corresponding to the dose amount of radiation exposure it is exposed to in use, wherein the patch has a perimeter that is devoid of outwardly extending loose lead wires.

62. A system according to claim 61, wherein the overlay material is configured to be integrated with the sensor patch.

63. A system according to claim 61, wherein the overlay material comprises a flexible, resilient, skin-like material.

64. A system according to claim 61, wherein the overlay material has a thickness of from about 0.5 to about 3 cm.

65. A system according to claim 61, wherein the overlay material has a thickness of from about 1 to about 1.5 cm.

66. An oncology single-use external use radiation dosimeter patch, the patch comprising a substantially conformable resilient substrate holding a circuit comprising at least one FET that changes a parameter in a detectable predictable manner when exposed to radiation, and wherein the patch comprises electronic memory that is configured to communicate with an external reader that electronically determines a radiation dose amount based on data from the patch and stores the radiation dose amount in the electronic memory, the body comprising opposing upper and lower primary surfaces, wherein the dosimeter patch, in use and position on a patient, is devoid of externally extending lead wires, and wherein the patch is a single-use self-contained dosimeter patch that is adhesively secured to skin of an oncology patient.

67. A dosimeter patch according to claim 66, wherein the lower primary surface comprises an adhesive thereon.

68. A dosimeter patch according to claim 66, wherein the patch comprises a coverlay that includes a medical grade adhesive that is configured to overlie the circuit substrate and hold the sensor patch in position on the patient.

69. A dosimeter patch according to claim 66, wherein the electronic memory is configured to store a date and time stamp of when the circuit FET threshold voltage was read by the external reader.

70. A dosimeter patch according to claim 69, wherein the electronic memory comprises an EEPROM.

71. A dosimeter patch according to claim 69, wherein the patch is at least one of pre-dosed and/or calibrated and predosing and/or calibration data is stored in the memory storage device.

72. A dosimeter patch according to claim 66, wherein the dosimeter patch is adapted to be inserted into a reader device and electrically couple the reader device to the patch circuit.

73. A dosimeter patch according to claim 66, wherein the circuit at least one FET is at least one MOSFET, wherein the circuit is adapted to engage with an external reader, and wherein the detectable operational parameter that changes is the at least one MOSFET threshold voltage.

74. A dosimeter patch according to claim 73, wherein the at least one MOSFET is configured to electrically short the gate to drain connection.

75. A dosimeter patch according to claim 66, wherein the circuit comprises at least two MOSFETS, a respective one positioned over another on opposing sides of the substrate in face-to-face alignment to inhibit orientation influence of the substrate.

76. A dosimeter patch according to claim 66, wherein the disposable patch is configured to communicate with a reader device wirelessly to obtain measured radiation data.

77. An oncologic external single-use radiation dosimeter patch, the patch comprising a substantially conformable resilient substrate holding a circuit with an operational electronic component that changes a parameter in a detectable predictable manner when exposed to radiation, the body comprising opposing upper and lower primary surfaces, wherein the dosimeter patch, in use, is devoid of externally extending lead wires and wherein the patch is a single-use dosimeter patch that is adhesively secured to the skin of a patient, wherein the at least one MOSFET is a pair of MOSFETs, wherein one of the MOSFETs in the pair is selectively implanted with dopant ions so as to shift its threshold voltage relative to that of the other MOSFET and/or to increase the sensitivity of the implanted MOSEET relative to the other MOSFET to thereby allow a differential voltage measurement to be obtained to measure radiation.

78. An oncology medical set-of single-use radiation dosimeter patches comprising:

a plurality of discrete single-use self-contained dosimeter patches, each patch comprising a substantially conformable resilient substrate holding a circuit with an operational electronic component that changes a parameter in a detectable predictable manner when exposed to radiation, wherein the patches comprise an electronic memory that engages an external reader to provide calibration data associated with the circuit components and that accepts and stores a calculated radiation dose associated with the patch, the body comprising opposing upper and lower primary surfaces, and wherein the dosimeter patch, in use, is devoid of externally hanging lead wires, and wherein the patches are configured to detect radiation doses in the range of at least from about 10 to about 200 cGy.

79. A set of patches according to claim 78, wherein the lower primary surfaces comprise an adhesive thereon, wherein the patches are substantially planar when viewed from the side, wherein the patches are held in a sterile package prior to use, and wherein at least some of the plurality of patches are used concurrently on a single patient.

80. A set of patches according to claim 78, wherein each patch in the set of patches comprises a coverlay that includes a medical grade adhesive that is configured to overlie the circuit substrate and hold the sensor patch in position on the patient.

81. A set of patches according to claim 78, wherein the sensor patches are configured with identifying indicia thereon, and wherein the electronic memory of the patches is configured to store a date and time stamp associated with when the external reader communicates with a respective patch.

82. A set of patches according to claim 81, wherein the operational electronic component is at least one MOSFET, and wherein the detectable operational parameter that changes is the at least one MOSFET threshold voltage.

83. A set of patches according to claim 78, wherein the calibration data comprises zero dose characterizing data of threshold voltage for the respective patch.

84. A set of patches according to claim 83, wherein the electronic memory is connected to a circuit that allows an external reader to communicate therewith to obtain a patient history record of radiation dose received by a patient during a radiation treatment session.

85. A set of patches according to claim 78, wherein the electronic memory is configured to store patient identification data transmitted by an external reader.

86. A set of patches according to claim 85 wherein each of the sensor patches are configured to detect radiation doses in the range of at least from about 40 to about 70 cGy, and wherein the sensor patches are stored in sterile packaging before use.

87. A set of patches according to claim 78, wherein the sensor patches are configured with a low profile when viewed from the side.

88. A set of patches according to 87, wherein the sensor patches are substantially planar when viewed from the side, and wherein the sensor patches are adhesively releasably attachable to the skin of the patient.

89. A set of patches according to claim 78, wherein the sensor patches are conformable to the skin and substantially planar.

90. A set of patches according to claim 78, wherein the sensor patches are adapted be at least partially inserted into a reader device and electrically connect the reader device to the circuit.

91. A set of patches according to claim 78, wherein the set of patches are disposed on a common sheet and wherein the sheet of patches is at least one of pre-dosed and/or calibrated before the set of patches are exposed to active therapeutic radiation.

92. A set of patches according to claim 91, wherein the set of patches are electrically coupled to each other during calibration and/or pre-dosing.

* * * * *

UNITED STATES PATENT AND TRADEMARK OFFICE

CERTIFICATE OF CORRECTION

PATENT NO. : 7,557,353 B2
APPLICATION NO. : 10/303591
DATED : July 7, 2009
INVENTOR(S) : Black et al.

It is certified that error appears in the above-identified patent and that said Letters Patent is hereby corrected as shown below:

Title Pages item 56:

Page 5, Right Column (line 40), “NASA Fact Sheet”:
Please correct “detecetor” to read -- detector --

Page 6 (line 7), “Sweeney et al.”:
Please correct “Visualization” to read -- Visualizing --

Page 6 (line 13), “Yang et al.”:
Please correct “Visualization” to read --Visualizing --

In the Claims:

Column 25, Claim 38, Line 30: Please correct “senor” to read -- sensor --

Column 25, Claim 39, Line 35: Please correct “patches. each” to read -- patches, each --

Column 26, Claim 56, Line 42: Please correct “patients” to read -- patient’s --

Column 28, Claim 77, Line 48: Please correct “MOSEET” to read -- MOSFET --

Column 28, Claim 78, Line 63:
Please correct “surfaces, and wherein” to read -- surfaces, wherein --

Signed and Sealed this

Fifteenth Day of September, 2009

David J. Kappos
*Director of the United States Patent and Trademark Office*